(12) United States Patent
Glenn et al.

(10) Patent No.: US 6,235,683 B1
(45) Date of Patent: *May 22, 2001

(54) METHOD FOR ENHANCED SUPERCOOLING OF PLANTS TO PROVIDE FROST PROTECTION

(75) Inventors: David Michael Glenn; Michael Wisniewski; Gary J. Puterka, all of Shepherdstown, WV (US); Dennis G. Sekutowski, Stockton, NJ (US)

(73) Assignees: Engelhard Corporation, Iselin, NJ (US); The United States of America as represented by the Secretary of Agriculture, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/410,283

(22) Filed: Sep. 30, 1999

Related U.S. Application Data

(63) Continuation-in-part of application No. 09/204,643, filed on Dec. 2, 1998, now Pat. No. 6,069,112, which is a continuation-in-part of application No. 08/972,659, filed on Nov. 18, 1997, now Pat. No. 6,110,867, which is a continuation-in-part of application No. 08/812,301, filed on Mar. 5, 1997, now Pat. No. 5,908,708.

(51) Int. Cl.$^7$ .......................... A01N 59/00; A01N 59/06; A01N 59/02
(52) U.S. Cl. ..................... 504/119; 120/126; 120/127; 120/187; 120/188; 71/DIG. 1
(58) Field of Search ............................. 504/119; 120/126, 120/127, 187, 188; 71/DIG. 1

(56) References Cited

U.S. PATENT DOCUMENTS

| | | | |
|---|---|---|---|
| 2,441,423 | 11/1948 | Elliot et al. | 260/29 |
| 2,733,160 | 1/1956 | Ller | 117/16 |
| 2,818,340 | 12/1957 | Goddin et al. | 99/2 |
| 2,948,632 | 8/1960 | Albert et al. | 514/465 |
| 3,120,445 | 2/1964 | Aluisi et al. | 106/286 |
| 3,124,505 | 3/1964 | Doyle et al. | 424/155 |
| 3,159,536 | 12/1964 | Marotta | 167/12 |
| 3,227,657 | 1/1966 | Haden et al. | 252/317 |
| 3,235,451 | 2/1966 | Odeneal | 167/42 |
| 3,346,507 | 10/1967 | Taulli | 252/316 |
| 3,964,649 | 6/1976 | Alexander | 222/399 |
| 4,071,374 | 1/1978 | Minton | 106/189 |
| 4,098,600 | 7/1978 | Chupp | 71/105 |
| 4,203,864 | 5/1980 | Sawyer et al. | 252/314 |
| 4,274,883 | 6/1981 | Lumbeck et al. | 106/308 |
| 4,279,895 | 7/1981 | Carle | 424/127 |
| 4,382,868 | 5/1983 | House | 252/28 |
| 4,484,409 | * 11/1984 | Caple et al. | 47/2 |
| 4,632,936 | 12/1986 | Boase et al. | 514/465 |
| 4,634,463 | 1/1987 | Ohsuga | 71/2 |
| 4,705,816 | 11/1987 | Pole | 43/52 |
| 5,122,518 | 6/1992 | Vrba | 514/63 |
| 5,186,935 | 2/1993 | Tucker | 424/410 |
| 5,392,559 | 2/1995 | Long | 43/52 |
| 5,393,461 | 2/1995 | Fillipova | 252/314 |
| 5,414,954 | 5/1995 | Long | 43/121 |
| 5,455,220 | 10/1995 | Dedolph | 504/241 |
| 5,480,638 | 1/1996 | Erwin | 424/614 |
| 5,656,571 | 8/1997 | Miller et al. | 504/116 |
| 6,069,112 | * 5/2000 | Glenn et al. | 504/119 |

FOREIGN PATENT DOCUMENTS

| | | | |
|---|---|---|---|
| 2005190A | 9/1970 | (DE) . | |
| 002067948 | 8/1974 | (DE) . | |
| 2926095 | 3/1980 | (DE) . | |
| 53-127134 | 11/1978 | (JP) | A01G/13/02 |
| 62-036142 | * 2/1987 | (JP) . | |
| 1792257A3 | 6/1990 | (SU) . | |
| WO9838866 | 2/1998 | (WO) | A01N/59/06 |

OTHER PUBLICATIONS

Section Ch, week 8403, Derwent Publications Ltd., London, GB, AN 84–014859, XP002069730 "Hydrophobic Silicic Acid Produce React Alkali Metal Silicate Mineral Acid Treat Product Silicone Oil" Nippon Silica Kogyo KK.

D.M. Glenn, et al. "Hydrophobic Particles For Pest Control in Deciduous Tree Fruit Production" XP002069729. Hortscience, vol. 32, No. 3, 1997, p. 467.

Section CH, week 7421, Derwent Publications Ltd., London, GB, An 74–38844V, XP002069731, "Water Repellent Coatings Based on Silica Fine Powder Paper Wood Concrete Mortar Gypsum Substrate", S. Shimoda.

Driggers, B. F. "Experiments with Talc and Other Dusts Used Against Recently Hatch Larvae of the Oriental and Codling Moths," J. Econ, Ent., 22 327–334 (1929).

Hunt, C.R., "Toxicity of Insecticide Dust Diluents and Carriers to Larvae of the Mexican Bean Beetle," J. Econ. Ent., 40 215–219 (1947).

P. Alexander, J.A. Kitchener and H.V.A. Briscoe, "Inert Dust Insecticides," Parts I, II, and III, Ann. Appl. Biol., 31 143–159 (1944).

W. Ebeling, R. F. Wagner "Rapid Desiccation of Drywood Termites with Inert Sorptive Dusts and Other Substances," J. Econ. Ent., 52 190–207 (1959).

M. Bar–Joseph, H. Frenkel "Spraying Citrus Plants with Kaolin Suspensions Reduces Colonization by The Spiraea Aphid," Crop Prot 2 371–374 (1983).

(List continued on next page.)

Primary Examiner—Jose' G. Dees
Assistant Examiner—Alton Pryor
(74) Attorney, Agent, or Firm—Raymond F. Keller

(57) ABSTRACT

In one embodiment, the present invention relates to a method for enhancing supercooling of a plant to temperatures below about −2° C., involving preventing the formation of ice crystals adjacent the plant by forming a substantially continuous hydrophobic membrane of particulate materials on portions of the plant capable of supporting droplets of water, the particulate material having a particle size distribution wherein up to about 90% by weight of the particles have a particle size of about 100 μm or less, and the substantially continuous hydrophobic membrane has a thickness from about 1 μm to about 1,000 μm.

23 Claims, 16 Drawing Sheets

OTHER PUBLICATIONS

Figure 1:
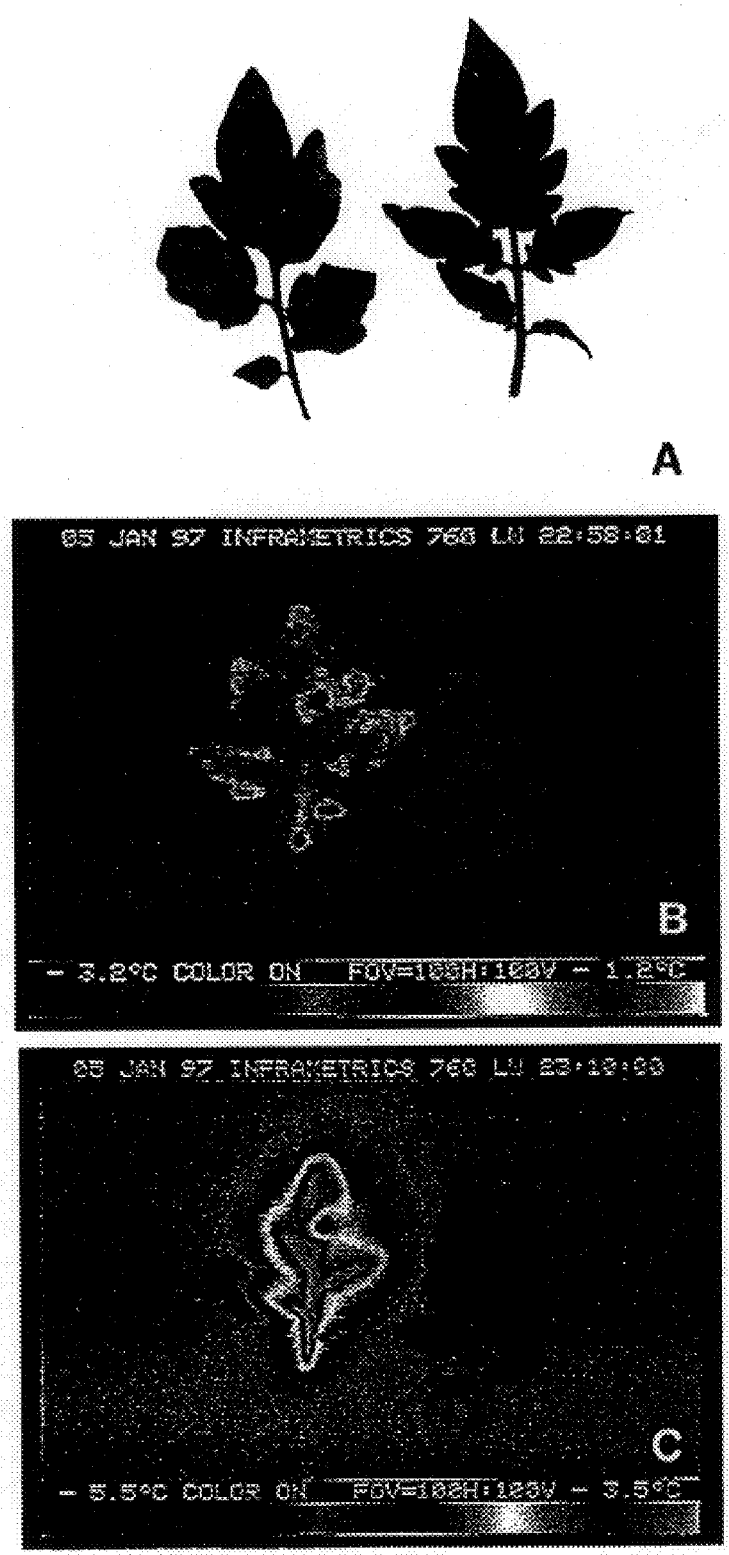

J.S. Dhaliwal, "Effect of Rainfall and Kaolinite Spray on the Corn Aphid, Rhopalosiphum Maidis (Fitch) Infesting Barley (Hordeum Vulgare Linn)," Forage Res. 5:155–157 (1979).

A. Boyce, "Mortality of Rhagoletis Completa Cress. (Diptera:Trypetidae) Through Ingestion of Certain Solid Materials," J. Econ. Ent., 25 1053–1059 (1932).

C. Richardson L. Glover, "Some Effects of Certain 'Inert' and Toxic Substances Upon the Twelve–Spotted Cucumber Beetle, Diabrotica Duodecimpunctata," J. Econ. Ent., 25 1176–1181 (1932).

A. Farmer, "The Effects of Dust on Vegetation: A Review," Envir Pol 79 (1193) 63–75.

V. Wigglesworth, "Action of Inert Dusts on Insects," Nature 153 (1944) 493–494.

W. David, B. Gardiner, "Factors Influencing the Action of Dust Insecticides," Bul Ent. Res. (1950) 41 1–61.

H. Kalmus, "Action of Inert Dusts on Insects," Nature 33 (1945) 188–189.

J. Kring, "Flight Behavior of Aphids," Ann Rev Ent. 17 461–493 (1972).

S. Chiu, Toxicity Studies of So–Called 'Inert' Materials with the Bean Weevil, Acanthoscelides Obtectus (Say) J. Econ. Ent. 32 240–248 (1939).

M. Baradas, B. Blad, N. Rosenberg, "Reflectant Induced Modification of Soybean Canopy Radiation Balance v. Longwave Radiation Balance," Agron J. 68 848–852 (1976).

G. Stanhill, S. Moreshet, M. Fuchs, "Effect of Increasing Foliage and Soil Reflectivity on the Yield and Water use Efficiency of Grain Sorghum," Agron J. 68 329–332 (1976).

S. Moreshet, S. Cohen, Y. Fuchs, "Effect of Increasing Foliage Reflectance on Yield, Growth and Physiological Behavior of a Dryland Cotton Crop," Crop Sci 19 863–868 (1979).

D. Eveling, "Similar Effects of Suspensions of Copper Oxychloride and Kaolin on Sprayed Leaves," Ann Apply Biol. (1972) 70, 245–249.

J. Jack, J. Gilbert, "The Effect of Suspended Clay on Ciliate Population Growth Rates," Freshwater Biol. (1993) 29, 385–394.

H. Uppal, S. Cheema, "Effect of Mulches and Kaolin Spray on Soil Temperature, Growth, Yield and Water Use of Barley," Ind J. Agric Sci (1981) 51, 653–659.

D. Meador, "Reducing Russet on 'Golden Delicious' Apples with Silicon Dioxide Formulation Foliage Sprays," Hort Sci (1977) 12, 504–505.

T. Babu, S. Hussaini, B. Satyanarayana, "Effect of Pre–Storage Seed Treatements on Adult Mortality, Oviposition and Development of Callosobruchus Chinensis L. (Bruchidae: Coleoptera) and the Viability of Mungbean (Vigana Radiata (L.) Wilczek) in India," Tropical Pest Mgt (1989) 35, 397–398.

T. Babu, S. Hussaini, M. Sriramulu, M. Siddiqui, Effect of Inert Clay and Insect Growth Regulators on the Development of Callosobruchus Chinesis L and the Germination of Mungbean Seed [Vigna Radiata(l)Wilczek].

R. Campbell, J. Ephgrave, "Effect of Bentonite Clay on the Growth of Gaeumannomyces Graminis var. tritici and on Its Interactions with Antagonistic Bacteria," J Gen Microbiol (1983) 129, 771–777.

J. Desmarchelier, C. Ahern, "Insecticide–Rententive Carriers 2. Fenitrothion–Impregnated Clays," Aus J Exper Agric (1988) 28, 271–8.

R. Wagner, W. Ebeling, "Lethality of Inert Dust Materials to Kalotermes Minor Hagen and Their Role as Preventivesin Structural Pest Control," J. Econ. Ent., (1959) 52, 208–212.

J.S. Kennedy, C.O. Booth, W.J.S. Kershaw, "Host Finding by Aphids In the Field," Ann Appl. Biol (1961), 49, 1–21.

W.O. Cline, R.D. Millholland, "Root Dip Treatments for Controlling Blueberry Stem Blight Caused by Botryosphaeria Dothidea in Container–Grown Nursery Plants," Plant Disease 76, 136–138 (1992).

J. Norman, "Development of Colletotrichum Gloesporioides f. sp. Clidemiae and *Septoria passiflorae* into Two Mycroherbicides with Extended Viability," Plant Disease 79, 1029–1032 (1995).

S. K. Bhattacharyya, M. K. Basu, "Kaolin Powder as a Fungal Carrier," Appl. Envir. Microbio. 44, 751–753 (1982).

R. H. Daines, R.J. Lukens, E. Brennan, I. Leone, "Phytotoxity of Captan as Influenced by Formulation, Environment and Plant Factors," Phytopathology (1957) 47, 567–572.

FDF Yougn, JRM Thacker, DJ Curtis, "The Effects of Three Adjuvants On the Retention of Insecticide Formulations by Cabbage Leaves,"J. Environ. Sci. Health (1996) B31, 165–178.

G. Haukenes, BK Hjeltns, "Kinetics of the Binding of Immunoglobulins, Antibodies and Virus Haemagglutination Inhibitors to Kaolin," Biologicals (1991) 19, 31–35.

J. Han, "Use of Antitranspirant Epidermal Coatings for Plant Protection in China," Plant Dis. (1990) 74, 263–266.

O. Ziv, RA Frederiksen, "The Effect of Film–Forming Anti–Transpirants on Leaf Rust and Powdery Mildew Incidence on Wheat," Plant Path (1987) 36, 242–245.

C. Jacob, et al. "New Strategies in the Control of Major Leaf Disease of Hevea," J. Myco & Plant Path (1195) 25, 120.

S. Marco, "Incidence of Nonpersistently Transmitted Viruses in Pepper Sprayed with Whitewash, Oil, and Insecticide, Alone or Combined," (1993) Plant Dis 77, 1119–1122.

Ziv, O. "Control of Septoria Leaf Blotch of Wheat and Powdery Mildew of Barley with Antitranspirant Epidermal Coating Materials," Phytopar (1983) 11, 33–38.

M. Kamp, "Control of Erysiphe Cichoracearum on Zinnia Elegans, with a Polymer–Based Antitranspirant," Hort Sci (1985) 20, 879–881.

J. Zekaria–Oren, Z Eyal, "Effect of Film–Forming Compounds on the Development of Leaf Rust on Wheat Seedlings," Plant Dis (1991) 75, 231–234.

A. Franck, M. Bar–Joseph, "Use of Netting and Whitewash Spray to Protect Papaya Plants Against Nivun Haamir (NH) Dieback Disease," Crop Prot (1992) 11, 525–528.

O. Ziv, "Effects of Bicarbonates and Film–Forming Polymers on Cucurbits Foliar Diseases," Plant Dis (1992) 76, 513–517.

TC Helvey, "Insecticidal effect of Inert Solid Diluents," Sci (1952) 116, 631–632.

HG Guy, HF Dietz "Further Investigations with Japanese Beetle Repellents," J. Econ. Ent., (1939) 32, 248–252.

Ccao, exia, A. Barbosa, "Combined Effects of Silica Aerognd Insowth Regulators Against Sitophilus Zeamans Motch Infestations," Int Cong Ent pro 1996.

MRGK Nair, "Structure of Waterproofing Epicuticular Layers in Insects in Relation to Inert Dust Action," Indian J. Ent. (1957) 19, 37–49.

BR Bartlett, "The Action of Certain 'Inert' Dust Materials on Parasitic Hymenoptera," J. Econ. Ent. (1951) 44, 891–896.

GL Hockenyos, "The Effect of Dusts on the Oriental Roach," J. Econ. Ent. (1933) 26, 792–794.

T. Hirano, M. Kiyota, I. Aiga, "Physical Effects of Dust on Leaf Physiology of Cucumber and Kidney Bean Plants," Envirn Poll (1995) 89, 255–261.

NKS Rao, "The Effects of Antitranspirants on Leaf Water Status, Stomatal Resistance and Yield in Tomato," J Hort Sci (1985) 60, 89–92.

DW Eveling MZ Eisa, "The Effects of a Cuticle–Damaging Kaolin On Herbicidal Phytotoxicity," Weed Res (1976) 16, 15–18.

S. Marco, O. Ziv, R. Cohen, "Suppression of Powdery Mildew in Squash by Applications of Whitewash, Clay and Antitranspirant Materials," Phytopar (1194) 22, 19–29.

SM Lipson, G. Stotzky, "Effect of Kaolinite on the Specific Infectivity of Reovirus," FEMS Micr. Let. 37, 83–88 (1986).

S. Lavie, G. Storzky, "Adhesion of the Clay Minerals Montmorillonite, Kaolinite, and Attapulgite reduces Respiration of Histoplasma Capsulatum," App & Envir Micro (1986) 51, 65–73.

MS Rajan, KR Reddy, RS Rao, GHS Reddi, "Effect of Antitranspirants and Reflectants on Pod Yield of Rainfed Groundnut," Agri Sci Dig (1981) 1, 205–206.

W. Ebeling, RJ Pence, "Termites and Other Enemies of Wood," Pest Cont. Oct. 1956, 46–64.

DW Eveling, A. Bataille, "The Effect of Deposits of Small Particles on the Resistance of Leaves and Petals to Water Loss," Envirn Poll (1984) 36, 229–238.

M. Llewellyn, J. Ervaz, "Abrasive Dusts as a Mechanism for Aphid Control," Ent. Exp. & Appl. 26 (1979) 219–222.

M. Swamiappan, S. Jayaraj, KC Chandy, "Effect of Activated Kaolinitic Clay on Some Storage Insects," Z. Ang. Ent. 80 (1976), 385–389.

D Permual, G. Le Patourel, Laboratory Evaluation of Acid–Activated Kaolin to Protect Stored Paddy Against Infestation by Stored Product Insects, J. Stored Prod. Res. 26, 149–153, 1990.

D Permual, G Le Patourel, "Small Bin Trials to Determine the Effectiveness of Acid–Activated Kaolin Against Four Species of Beetles Infesting Paddy Under Tropical Storage Conditions," J. Stored Prod. Res. 28, 193–199 (1992).

DT Lowery, MK Sears, CS Harmer, "Control of Turnip Mosaic Virus of Rutabaga With Applications of Oil, Whitewash, and Insecticides," J. Econ. Ent. (1990) 83, 2352–2356.

S. Marco, "Incidence of Aphid–Transmitted Virus Infections Reduced by Whitewash Sprays on Plants," Amer, Phytop (1986) 76, 1344–1348.

J. Basnizki, M. Evenari, "The Influence of a Reflectant on Leaf Temperature and Development of the Globe Artichoke (*Cynara scolymus L.*)," J. Am Soc Hort Sci 100, 109–112 (1975).

EF Durner, TJ Gianfagna, "Interactions of Ethephon, Whitewashing, and Dormant Oil on Peach Pistil Growth, Hardiness and Yield," Am Hort Sci 27, 104–105 (1992).

EF Durner, TJ Gianfagna, "Peach Pistil Growth Inhibition and Subsequent Bloom Delay by Midwinter Bud Whitewashing," Am Hort Sci 25, 1222–1224 (1990).

WJ Lipton, "Temperatures and Net Heat Gain in Normal and Whitewashed Cantaloupe Fruits," J. Amer. Hort. Sci. 97, 242–244 (1972).

WJ Lipton, F. Matoba, "Whitewashing to Prevent Sunburn of 'Crenshaw' Melons," Hortscience, 6, 343–345 (1971).

WS Cranshaw, DJ Liewehr, "Effects of Colored Sprays on Aphid & Psyllid Colonization," SW Entomol 15, 205–209 (1990).

S. Marco, "Possible Modes of Action of Whitewash in Reducing Virus Incidence in Potatoes," Potato Res 33, 138–139 (1990).

I. Bar–Zakay, M. Gokkes, Y. Oren, "Chemical Control of Aphids on Citrus Bearing Trees," Phytoparasitica 15, 343 (1987).

S. Marco, "Reducing the Incidence of Aphid–Transmitted Viruses by Reflective Materials," Phytoparasitica 13, 279–280 (1985).

DJ Gumpf, GN Oldfield, RK Yokomi, "Progress in the Control of Citrus Stubborn Disease," Proc Int. Soc. Citric, 457–458 (1981).

CG Summers, JJ Stapleton, AS Duncan, DA Hart, "Comparison of Sprayable and Film Mulches in Delaying the Onset of Aphid–Transmitted Virus Diseases in Zucchini Squash," Plant Dis (1995) 79, 1126–1131.

PC Nicot, M. Mermier, BE Vaissiere, J. Lagier, "Differential Spore Production for Botrytis Cinerea on Agar Medium and Plant Tissue Under Near–Ultraviolet Light–Absorbing Polyethylene Film," Plant Dis (1196) 80, 555–558.

JJ Stapleton, WK Asai, JE DeVay, "Use of Polymer Mulches in Integrated Pest Management Programs for Establishment of Perennial Fruit Crops," (1989) Acta Hort. 255, 161–168.

RE Byers, CG Lyons, "Effect of Chemical Deposits from Spraying Adjacent Rows on Efficacy of Peach Bloom Thinners," HortSci (1985) 20, 1076–1078.

RE Byers, KS Yoder, GE Mattus, "Reduction in Russetting of 'Golden Delicious' Apples with 2, 4, 5–TP and Other Compounds," HortScience 18:63–65 (1983).

RE Byers, DH Carbaugh, CN Presley, "'Stayman' Fruit Cracking as Affected by Surfactants, Plant Growth Regulators, and Other Chemicals," J. Amer. Soc. Hort. Sci. 155:405–411 (1990).

\* cited by examiner

M96-Dust-Water-Oil-Methanol

Supercote/Dust

Figure 8:
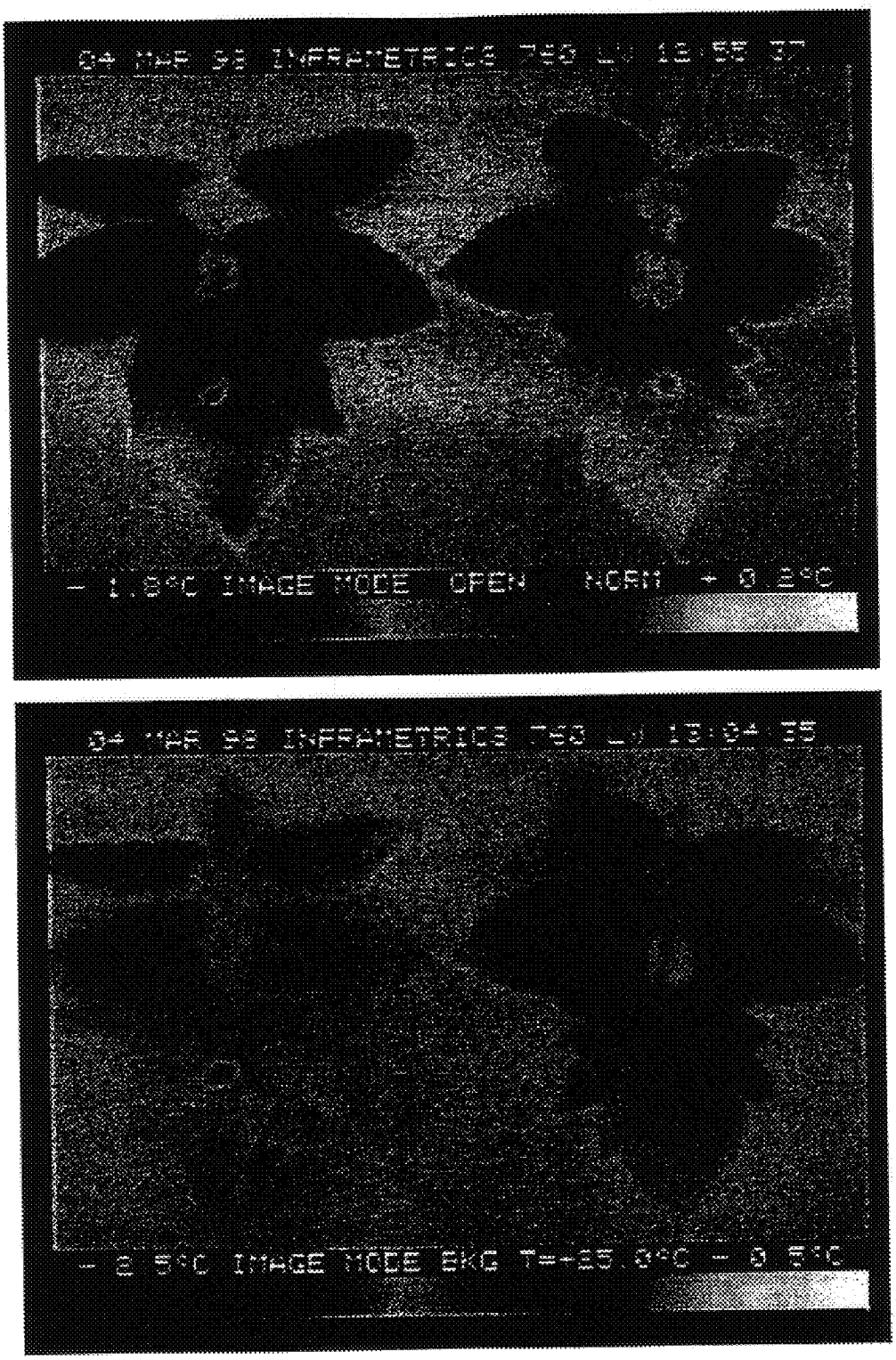

Supercote/Methanol FIG. 8

Figure 9:
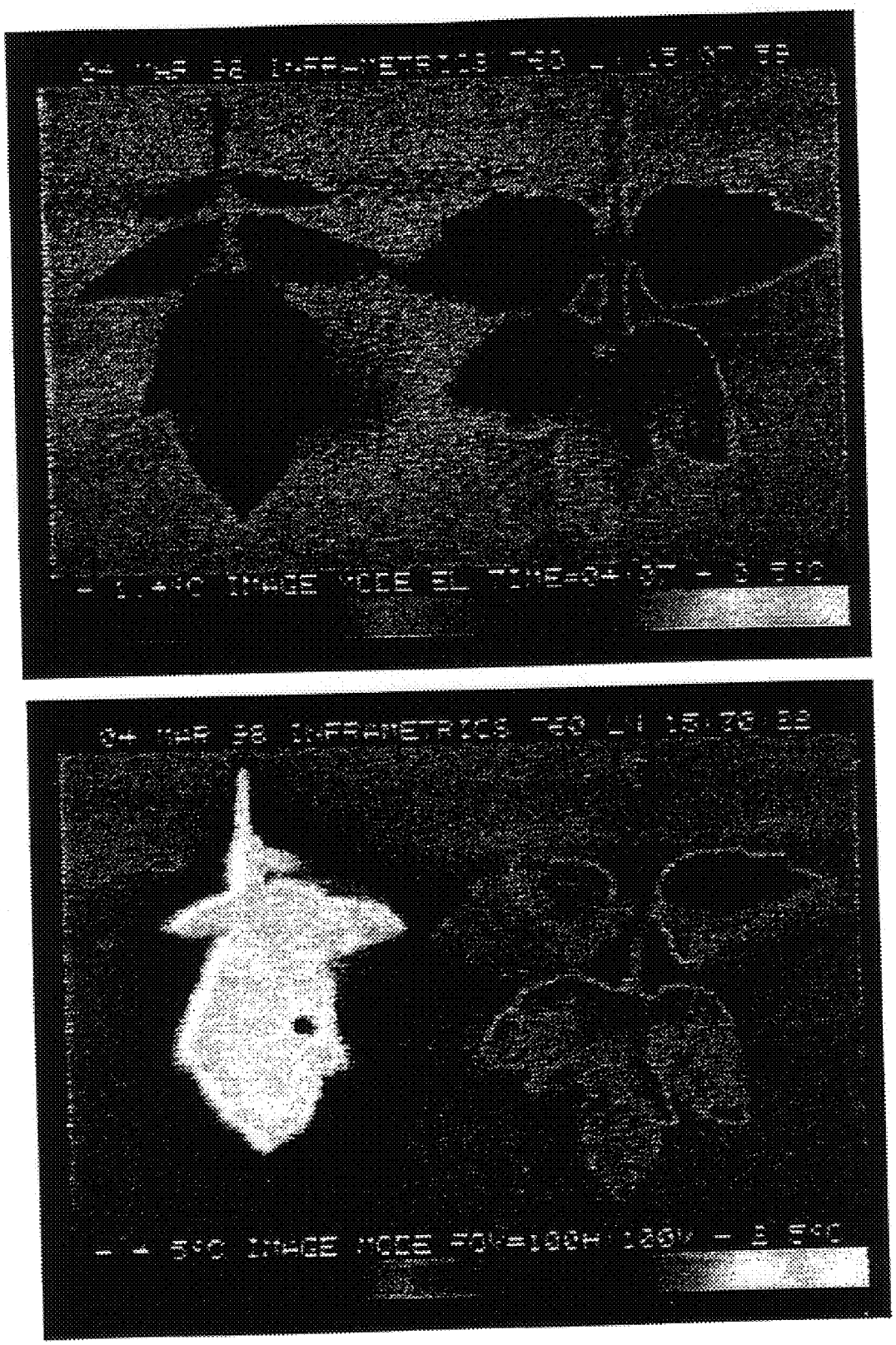

Supercote/Oil     FIG. 9

Figure 10:
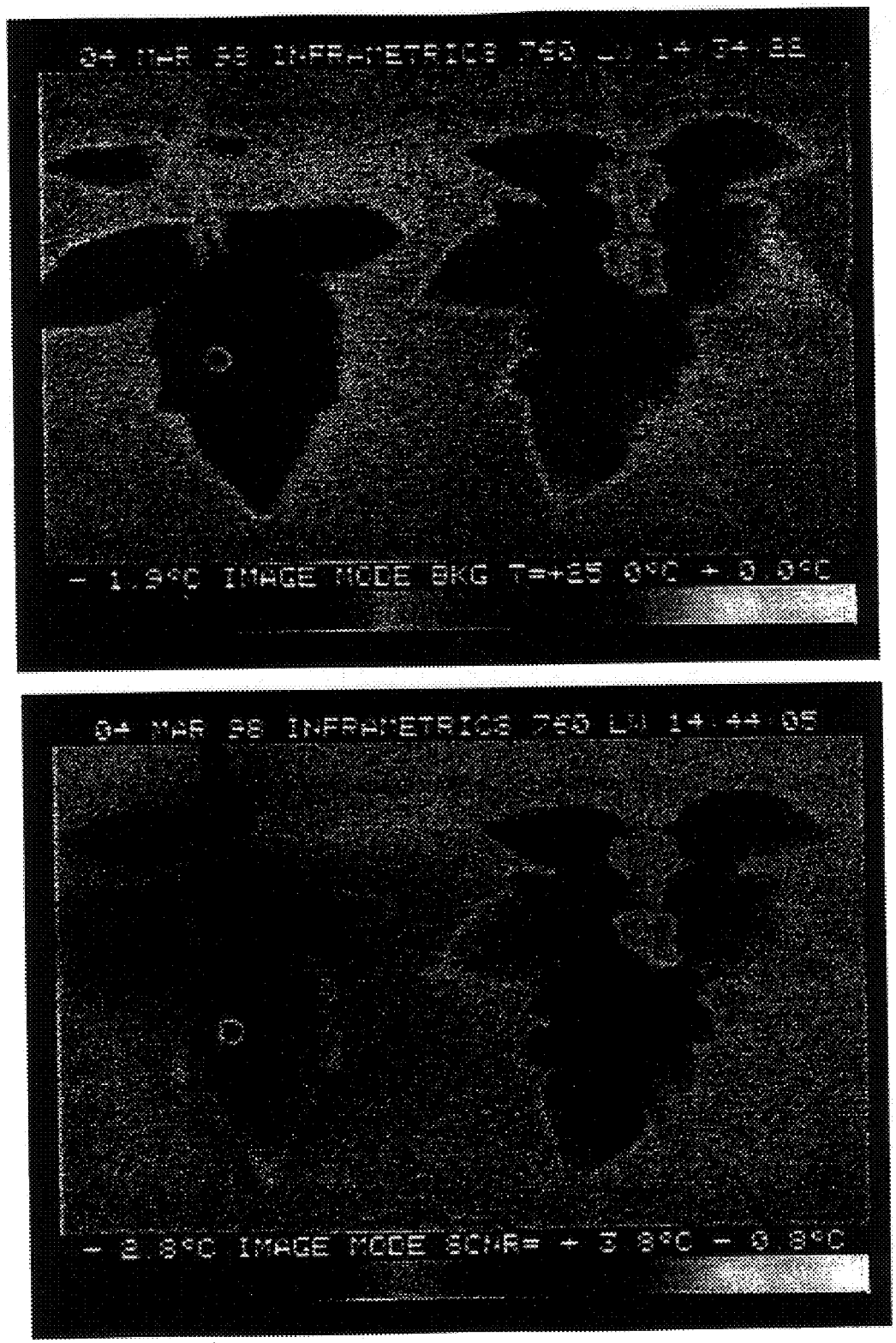

Supercote/Water  FIG. 10

M96-Methanol

M96-Oil

M96-Water

Figure 14:
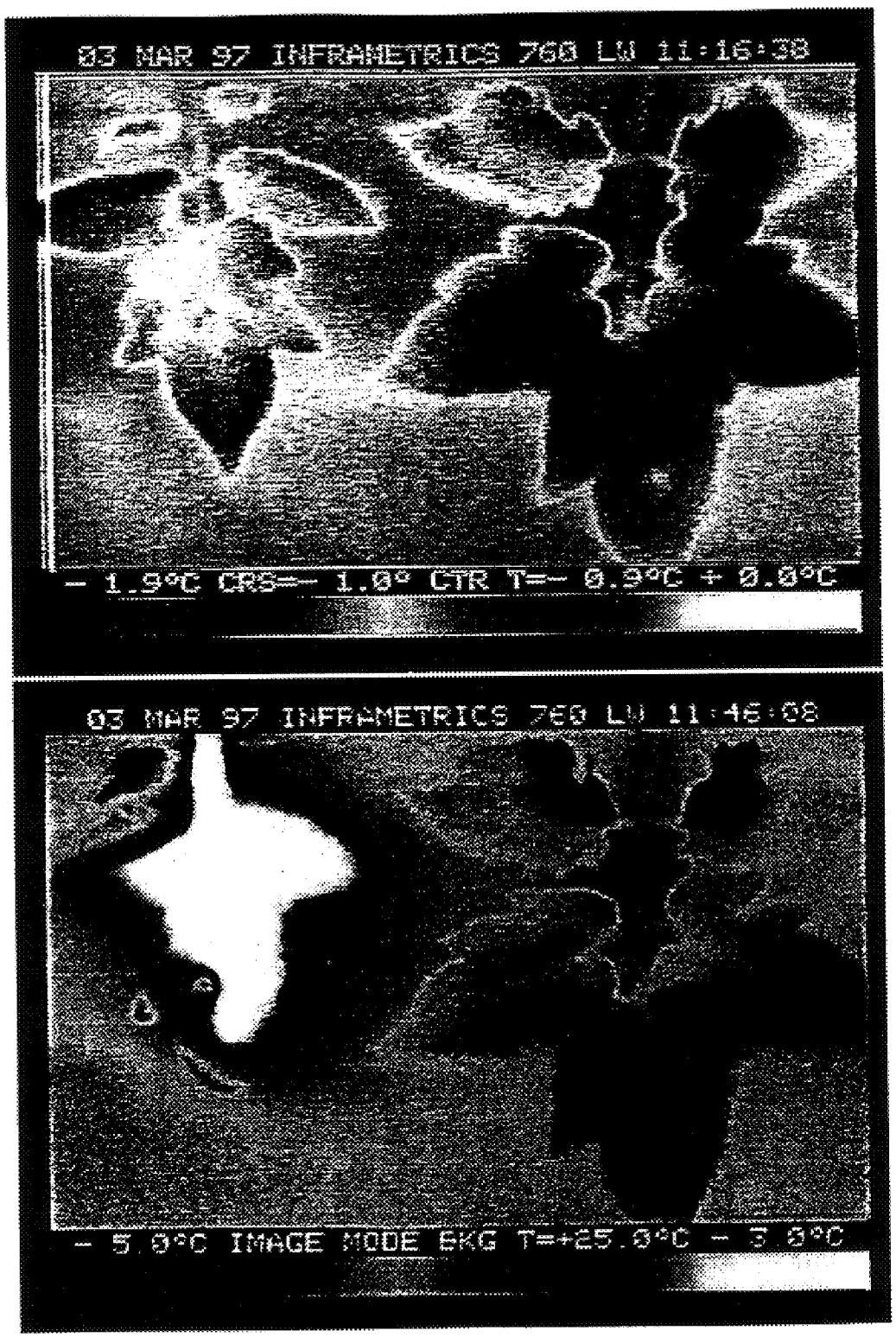

M96-Dust FIG. 14

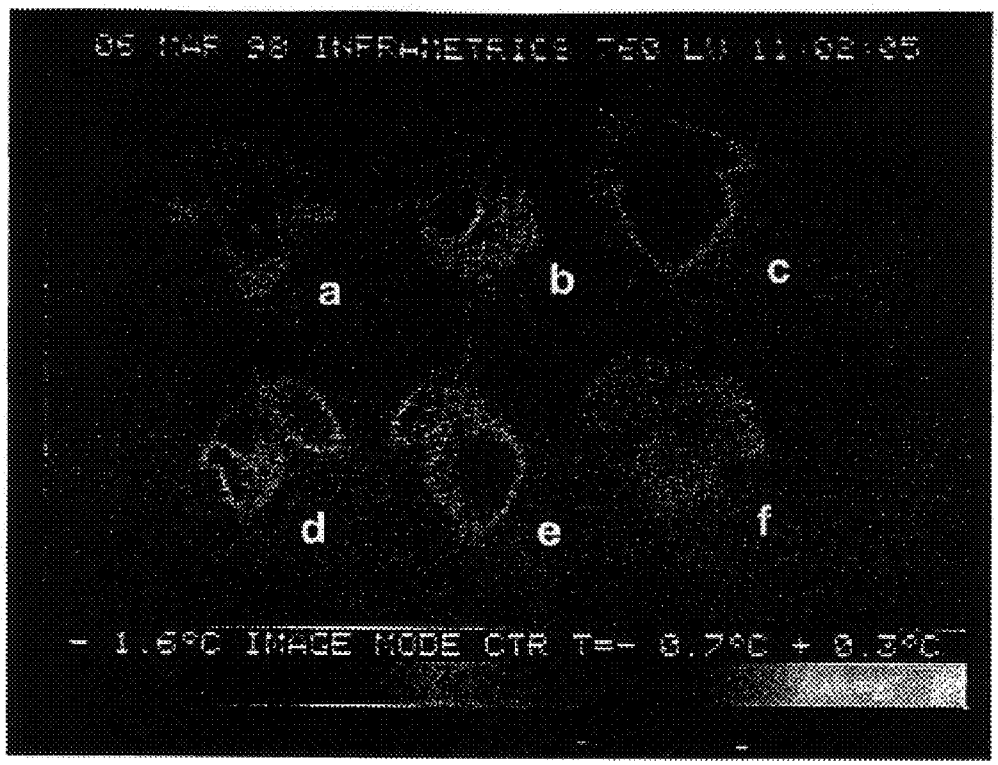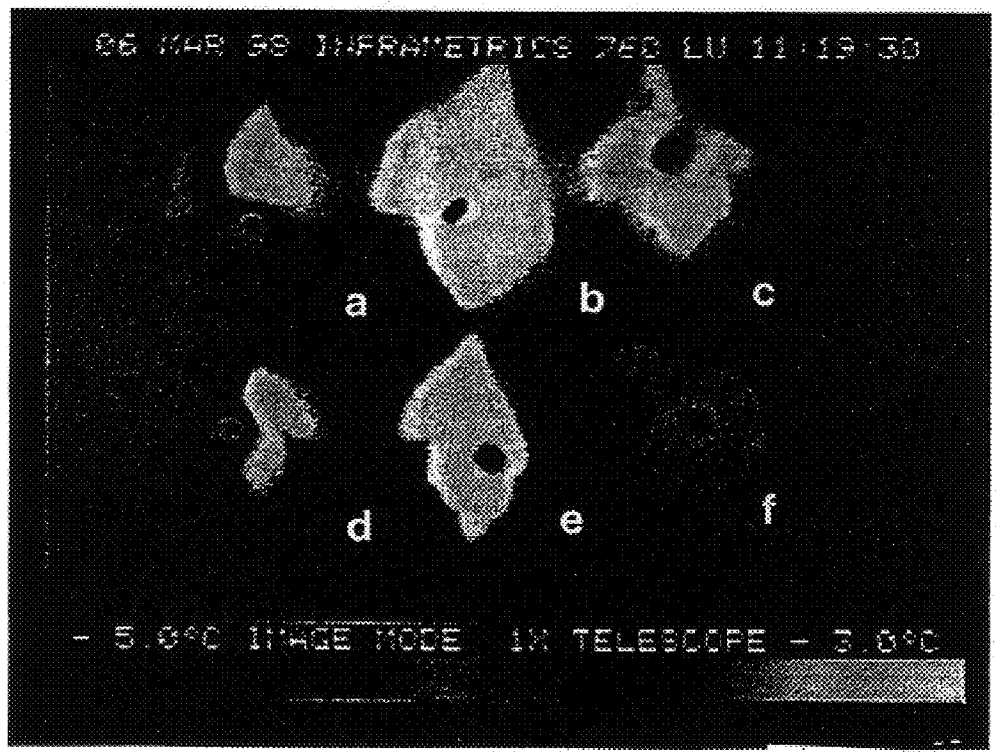
FIG. 16

METHOD FOR ENHANCED SUPERCOOLING OF PLANTS TO PROVIDE FROST PROTECTION

CROSS-REFERENCE TO RELATED APPLICATIONS

This application is a continuation-in-part of U.S. patent application Ser. No. 09/204,643, filed Dec. 2, 1998, now U.S. Pat. No. 6,069,112 which is a continuation-in-part of U.S. patent application Ser. No. 08/972,659, filed Nov. 18, 1997, now U.S. Pat. No. 6,110,867 which is a continuation-in-part of U.S. patent application Ser. No. 08/812,301, filed Mar. 5, 1997, now U.S. Pat. No. 5,968,708 all of which are incorporated herein by reference for their teachings related to the invention disclosed herein.

TECHNICAL FIELD

The present invention is directed to a method for enhancing the supercooling of plants to prevent freezing damage.

BACKGROUND OF THE INVENTION

"The objective of having an inexpensive material that can be stored easily until needed, applied easily, and provide frost protection has existed since the mid 1950's. Many materials have been examined. These fall into several categories but generally, they have been materials that allegedly either changed the freezing point of the plant tissue; reduced the ice-nucleating bacteria on the crop, thereby inhibiting ice and frost formation; or affected growth, i.e. delayed dehardening or work by some 'unknown mode of action'. To our knowledge, no commercially available material has successfully withstood the scrutiny of a scientific test." (K. B. Perry, 1998, Basics of Frost and Freeze protection for horticultural crops). HortTechnology 8(1):10–15. See also Warmund et al, Advances in Strawberry Research 1994, pages 20–25, who also found no significant effect of a frost protectant chemical. As stated by Perry (1998) there are four areas of chemical development related to frost protection: 1) materials that change the freezing point of the plant tissue or water; 2) reduce the populations of ice nucleating bacteria on the crop surface, thereby inhibiting ice formation on the crop surface; 3) delay dehardening; 4) genetic engineering to increase cold hardiness.

Patents related to the first area of technology include: Barr et al U.S. Pat. No. 5,133,891, which relates to treatment of plants for frost protection by the application of an organic chemical; Shin et al U.S. Pat. No. 5,276,006, which relates to a cryoprotectant composition that increases the tissue resistance to freeze damage; Savignano et al U.S. Pat. No. 5,653,054 which relates to a process for preventing frost formation on plants that involves lowering the freezing point of water; Lengyel U.S. Pat. No. 4,597,883 which relates to a composition and method for minimizing frost damage to plants that includes a salt-based solution to lower the freezing point of water and resist cell damage to freezing temperature; Artozon U.S. Pat. No. 5,618,330 which relates to plant treatment compositions and processes that involve high concentrations of salts to protect against frost damage; and Suslow et al U.S. Pat. No. 5,633,450 which relates to chitinase-producing plants that are resistant to cold damage.

Patents related to the second area of technology include: Lindow U.S. Pat. No. 4,432,160 which relates to the microbial inhibition of frost damage to plants which is a method involving the selection and use of ice nucleating deficient bacteria to prevent freezing damage; and Orser et al. U.S. Pat. No. 4,766,077 which relates to ice nucleation deficient microorganisms made by genetic manipulation which involves a method to produce ice nucleating deficient organisms for application to plants as a frost protectant.

The third area of technology does not directly prevent frost damage, but instead delays the development of frost-sensitive reproductive tissues in the early growing season so that frost does not occur when frost-sensitive tissues are exposed. There are also non-chemical approaches to frost protection that include Muscatell U.S. Pat. No. 4,434,345 which relates to a microwave system for frost protection of fruit trees that generates heat to prevent freezing, and Donohue et al U.S. Pat. No. 4,901,472, which relates to a method and apparatus for the protection of citrus trees from frost damage using an insulating pad for the trunk of the tree. M. Wisniewski and M. Fuller (Ice nucleation and deep supercooling: new insights using infrared thermography in: *Cold Adapted Organisms: Fundamentals and Applications*. Eds. R. Margesin and F. Schinner, Landes BioScience, Austin, Tex.) indicate that the application of a silicone grease to plant surfaces makes a water repellant film that prevents ice from propagating into the plant and allows the plant to supercool, thus preventing frost damage. However, the application of silicon grease to plants is phytotoxic since it prevents the exchange of gases to and from the leaf. Therefore, there is still a need for a cost effective, nontoxic agent to prevent freezing damage that does not interfere with the exchange of gases, or other physiological processes of plants, and particularly horticultural crops.

The fourth area of technology relates to genetic engineering of plants to increase their tolerance to cold. Caceci et al U.S. Pat. No. 5,932,697 and U.S. Pat. No. 5,925,540 relate to methods of synthesizing a peptide that increases cold hardiness. Guy et al U.S. Pat. No. 5,837,545 relates to a method of synthesizing polypeptides to increase cold hardiness.

SUMMARY OF THE INVENTION

In one embodiment, the present invention relates to a method for enhancing supercooling of a plant to temperatures below about $-2°$ C., involving preventing the formation of ice crystals adjacent the plant by forming a substantially continuous hydrophobic membrane of particulate materials on portions of the plant capable of supporting droplets of water, the particulate material having a particle size distribution wherein up to about 90% by weight of the particles have a particle size of about 100 $\mu$m or less, and the substantially continuous hydrophobic membrane has a thickness from about 1 $\mu$m to about 1,000 $\mu$m.

In another embodiment, the present invention relates to a method for enhancing the supercooling of a horticultural crop to temperatures below about $-3°$ C., involving preventing the formation of ice crystals adjacent the horticultural crop by applying a slurry comprising particulate materials and a liquid on portions of the horticultural crop capable of supporting droplets of water; and permitting the liquid to evaporate thereby forming a substantially continuous hydrophobic membrane of particulate materials on the horticultural crop, the particulate material having a particle size distribution wherein up to about 90% by weight of the particles have a particle size of about 10 $\mu$m or less, and the substantially continuous hydrophobic membrane has a thickness from about 3 $\mu$m to about 750 $\mu$m.

In yet another embodiment, the present invention relates to a method for enhancing the supercooling of a horticultural crop to temperatures below about $-4°$ C., involving preventing the formation of ice crystals adjacent the horticultural crop by applying a slurry comprising particulate materials, a liquid, and an adjuvant on portions of the horticultural crop capable of supporting droplets of water; and permitting the liquid to evaporate thereby forming a substantially continuous hydrophobic membrane of particulate materials on the horticultural crop, the particulate material having a particle size distribution wherein up to about 90% by weight of the particles have a particle size of about 10 μm or less, and the substantially continuous hydrophobic membrane comprises from about 25 to about 5000 micrograms of particulate material/$cm^2$ of horticultural crop surface.

In still yet another embodiment, the present invention relates to a method for enhancing supercooling of a plant to temperatures below about −2° C., involving preventing the formation of ice crystals adjacent the plant by forming a substantially continuous hydrophobic membrane of particulate materials entrained with air on at least a portion of the plant capable of supporting droplets of water, the particulate material having a particle size distribution wherein up to about 90% by weight of the particles have a particle size of about 100 μm or less, and the substantially continuous hydrophobic membrane has a thickness from about 100 μm to about 10,000 μm.

SUMMARY OF THE DRAWINGS

FIGS. 1A–1C are pictures representing leaves treated in accordance with Example 3.

FIGS. 2A–2C are pictures representing leaves treated in accordance with Example 4.

FIG. 3 illustrates coverage on leaf surfaces with various materials and formulations.

FIG. 4 illustrates coverage on leaf surfaces with various materials and formulations.

FIG. 5 illustrates coverage on leaf surfaces with various materials and formulations.

FIG. 6 illustrates coverage on leaf surfaces with various materials and formulations.

FIG. 7 illustrates treated leaves and untreated leaves with regard to freezing.

FIG. 8 illustrates treated leaves and untreated leaves with regard to freezing.

FIG. 9 illustrates treated leaves and untreated leaves with regard to freezing.

FIG. 10 illustrates treated leaves and untreated leaves with regard to freezing.

FIG. 11 illustrates treated leaves and untreated leaves with regard to freezing.

FIG. 12 illustrates treated leaves and untreated leaves with regard to freezing.

FIG. 13 illustrates treated leaves and untreated leaves with regard to freezing.

FIG. 14 illustrates treated leaves and untreated leaves with regard to freezing.

FIG. 15 illustrates the freezing of treated and untreated leaves.

FIG. 16 illustrates the freezing of treated and untreated leaves.

DETAILED DESCRIPTION OF THE INVENTION

"Supercooling" as used herein is a physical phenomenon in which liquid water cools to temperatures below 0° C. without the formation of ice. Ice is prevented from forming because ice nuclei, needed to induce freezing, are absent or the water is isolated from these ice nuclei. Supercooling in plants is a desirable phenomenon since it is not the freezing temperature per se that causes damage, but rather the formation of ice crystals on/in the plant(s) that damages and kills plant tissues by dessication and/or physical disruption of the cells.

The plants that may be treated in accordance with the present invention include horticultural crops and especially actively growing agricultural crops, actively growing ornamental crops, fruiting agricultural crops and fruiting ornamental crops and the products thereof. Agricultural crops are plants used to make useful products, such as food products, feed products, fiber products and the like. Ornamental crops are plants used for decoration or aesthetic reasons.

General examples of plants include fruits, vegetables, trees, flowers, shrubs, bushes, grasses, roots, seeds and other landscape plants and ornamental plants. Any portion of a plant may be treated in accordance with the present invention including leaves, branches, stems, trunks, buds, flowers, and fruits, whether or not they are in the dormant or growing state. Specific examples that may be treated in accordance with the present invention include pear trees, apple trees, orange trees, grapefruit trees, tangerine trees, nectarine trees, peach trees, cherry trees, plum trees, lemon trees, apricot trees, raspberry plants, strawberry plants, blueberry plants, blackberry plants, tomato plants, corn, beans including soybeans, squash, tobacco, roses, violets, tulips and so on.

The present invention generally involves applying particulate materials to plants which provides or enhances the supercooling characteristics of the plants thereby preventing the formation of ice crystals on the plants at temperatures below 0° C. at atmospheric pressure.

In one embodiment, the methods of the present invention prevent the formation of ice crystals on treated plants at temperatures below about −2° C. at atmospheric pressure. In another embodiment, the methods of the present invention prevent the formation of ice crystals on treated plants at temperatures below about −3° C. at atmospheric pressure. In yet another embodiment, the methods of the present invention prevent the formation of ice crystals on treated plants at temperatures below about −4° C. at atmospheric pressure. In a preferred embodiment, the methods of the present invention prevent the formation of ice crystals on treated plants at temperatures below about −5° C. at atmospheric pressure. In another embodiment, the methods of the present invention prevent the formation of ice crystals on treated plants at temperatures at or below about −6° C. at atmospheric pressure.

The particulate materials suitable for use in the present invention are hydrophobic. In one embodiment, the particulate materials are hydrophobic in and of themselves, (for example, mineral talc). In another embodiment, the particulate materials are hydrophilic materials that are rendered hydrophobic by application of an outer coating of a suitable hydrophobic wetting agent or coupling agent (for example, in an embodiment where a particulate material has a hydrophilic core and a hydrophobic outer surface).

Examples of hydrophobic materials include mineral talc. Examples of particulate hydrophilic materials that are rendered hydrophobic by application of an outer coating of a suitable hydrophobic wetting agent or coupling agent include minerals, such as calcium carbonate, talc, kaolin (both hydrous kaolins and calcined kaolins, with calcined kaolins being preferred), bentonites, clays, pyrophyllite, dolomite, silica, feldspar, sand, quartz, chalk, limestone, precipitated calcium carbonate, diatomaceous earth and barytes; functional fillers such as aluminum trihydrate, pyrogenic silica, and titanium dioxide.

The surfaces of particulate hydrophilic materials can be made hydrophobic by contact with at least one hydrophobic wetting agent or a coupling agent. Industrial mineral applications, especially in organic systems such as plastic composites, films, organic coatings or rubbers, utilize hydrophobic surface treatments to render a mineral surface hydrophobic; see, for example, Jesse Edenbaum, *Plastics Additives and Modifiers Handbook*, Van Nostrand Reinhold, New York, 1992, pages 497–500, which is incorporated herein by reference for teachings of such hydrophobic surface treatment materials and their application.

Coupling agents such as fatty acid compounds and silane compounds may be used to surface treat solid particles to render the surfaces hydrophobic. Such hydrophobic agents are known in the art. Examples include organic titanates available under the trade designation Tilcom® from Tioxide Chemicals; organic zirconate or aluminate coupling agents available from Kenrich Petrochemical, Inc.; organofunctional silanes such as vinyltriethoxysilane, vinyl tris-(2-methoxyethoxy)silane, γ-methacryloxypropyltrimethoxysilane, β-(3,4-epoxycyclohexyl)ethyltrimethoxysilane, γ-glycidoxypropyltrimethoxysilane, γ-mercaptopropyltrimethoxysilane, γ-aminopropyltriethoxysilane, N-β-(aminoethyl)-γ-aminopropyltrimethoxysilane, and β-mercaptoethyltriethoxysilane, and others available under the trade designation Silquest® from Witco or Prosil® from PCR; modified silicone fluids such as the DM-Fluids available from Shin Etsu; and fatty acids such as double pressed stearic acid and triple pressed stearic acid and others available under the trade designation Hystrene® or Industrene® from Witco Corporation or Emersol® products from Henkel Corporation. In a preferred embodiment, stearic acid and stearate salts are particularly effective for rendering a particle surface hydrophobic.

Examples of preferred particulate materials suitable for use in the present invention that are commercially available include siloxane treated calcined kaolins available under the trade designation Translink® from Engelhard Corporation, Iselin, N.J.; and calcium carbonate available under the trade designations Supercoat®.

The particulate materials suitable for use in the present invention are finely divided. The term finely divided as used herein means that the particulate materials have a median individual particle size (average diameter) below about 100 microns. In one embodiment, the particulate materials have a median individual particle size of about 10 microns or less. In another embodiment, the particulate materials have a median individual particle size of about 3 microns or less. In yet another embodiment, the particulate materials have a median individual particle size of about 1 micron or less.

Particle size and particle size distribution as used herein are measured with a Micromeritics Sedigraph 5100 Particle Size Analyzer. Measurements are recorded in deionized water for hydrophilic particles. Dispersions are prepared by weighing 4 grams of dry sample into a plastic beaker, adding a suitable dispersant and diluting to the 80 ml mark with deionized water. The slurries are then stirred and set in an ultrasonic bath for 290 seconds. Typically, a 0.5% tetrasodium pyrophosphate is used as a dispersant for kaolin; and a 1.0% Calgon T is used for calcium carbonate. Typical densities for the various powders are programmed into the sedigraph, for example, 2.58 g/ml for kaolin. The sample cells are filled with the sample slurries and the X-rays are recorded and converted to particle size distribution curves by the Stokes equation. The median particle size is determined at the 50% level.

In a preferred embodiment, the particulate material has a particle size distribution wherein at least about 90% by weight of the particles have a particle size of under about 100 microns. In another embodiment, the particulate material has a particle size distribution wherein at least about 90% by weight of the particles have a particle size of about 10 microns or less. In yet another embodiment, the particulate material has a particle size distribution wherein at least about 90% by weight of the particles have a particle size of about 3 microns or less. In still yet another embodiment, the particulate material has a particle size distribution wherein at least about 90% by weight of the particles have a particle size of about 1 micron or less.

The surface of a plant is treated with a suitable amount of one or more particulate materials that is effective in enhancing the supercooling characteristics of the plant. The amount of particulate materials varies depending upon a number of factors, such as the identity of the particulate material, the type of plant, the temperature at which the formation of ice crystals are desired not to form (for example, −2° C. or −4° C.), and the like. The amount of particulate material applied to a plant to enhance supercooling can be determined by one skilled in the art. The particulate materials are applied to a plant so that all or a portion of the surface of the plant is covered. Covering only a portion of the plant can be effective, for example, since neither the under surface of the plant (that which is not exposed directly to a source of water which may freeze, such as dew) need not be treated in accordance with the present invention. Although full plant coverage can reduce the frequency of sites where ice nucleation can occur, complete coverage of the plant is unnecessary in some instances (it is preferable to cover at least a substantial portion of the upper surface of the plant).

The application of particulate materials in accordance with the present invention results in the formation of a residue, foam, membrane or film of one or more layers of particulate materials on the plant surface. In some instances herein, use of any one of the terms residue, foam, membrane or film includes the other three terms. The amount of particulate materials is sufficient to fully or partially coat the plant surface and make the plant surface water-repellent. Various environmental conditions, such as wind and rain, may reduce the amount of the particulate materials on plants and therefore, it is preferable in certain instances to apply the particles one or more times during the frost-prone growing season of the plant in order to maintain the desired frost prevention effects of the present invention.

After the particulate materials are applied to a plant, the slurry is permitted to dry (the volatile liquids evaporate) in embodiments where the particulate materials are applied via a slurry, wherein a continuous or substantially continuous hydrophobic film of the particulate materials is formed. By continuous (or substantially continuous), it is meant that, where applied, the dry film is continuous (or substantially continuous). For example, in an embodiment where the upper third of a fruit is covered with particulate material in accordance with the present invention, the film covering the upper third of the fruit is continuous or substantially continuous while the bottom two-thirds of the fruit is not covered with the particulate material. Similarly, in an embodiment where the top surface or sky facing portion of a leaf is covered with particulate material in accordance with the present invention, the film covering the top surface or sky facing portion of a leaf is continuous or substantially continuous while the underside or ground facing portion of a leaf is not covered with the particulate material. Typically, the portions of the plant surface covered or treated in accordance with the present invention include those which are capable of supporting a droplet of water thereby minimizing and/or preventing contact between water and the plant surface. By preventing the presence or accumulation of droplets of water on the surface of plants, the formation of ice crystals and/or ice nucleation sites is minimized and/or eliminated.

Of the covered portion of a plant surface, the particulate material film is substantially continuous in that it covers from about 75% to about 100% of the surface area, thus the openings or noncontinuous areas the particulate material film constitutes from about 0% to about 25% of the surface area. In another embodiment, the particulate material film is substantially continuous in that it covers from about 90% to about 99.9% of the coated surface area, thus the openings or noncontinuous areas the particulate material film constitutes from about 0.1% to about 10% of the coated surface area. In yet another embodiment, the particulate material film is substantially continuous in that it covers from about 95% to about 99% of the coated surface area, thus the openings or noncontinuous areas the particulate material film constitutes from about 5% to about 1% of the coated surface area.

In the substantially continuous particulate material film, the maximum average size (average diameter) of the openings, voids or noncontinuous areas in the film is generally less than about 100 $\mu$m. In another embodiment, the maximum average size of openings or noncontinuous areas in the particulate material film is generally less than about 10 $\mu$m. In yet another embodiment, the maximum average size of openings or noncontinuous areas in the particulate material film is generally less than about 5 $\mu$m.

The thickness of the particulate material film applied ranges from about 1 $\mu$m or 100 $\mu$m to about 10,000 $\mu$m. In another embodiment, the thickness of the particulate material film ranges from about 3 $\mu$m to about 1,000 $\mu$m. In yet another embodiment, the thickness of the particulate material film ranges from about 5 $\mu$m to about 500 $\mu$m.

In a preferred embodiment, an amount of particulate material is applied so that the portion of the plant surface covered is white or transparent in appearance. In one embodiment, from about 25 to about 5000 micrograms of particulate material/$cm^2$ of plant surface for particles having a specific density of around 2–3 g/$cm^3$ is applied to fully or partially coat the plant surface. In another embodiment, from about 50 to about 3000 micrograms of particulate material/$cm^2$ of plant surface for particles having a specific density of around 2–3 g/$cm^3$ is applied to fully or partially coat the plant surface. In yet another embodiment, from about 100 to about 500 micrograms of particulate material/$cm^2$ of plant surface for particles having a specific density of around 2–3 g/$cm^3$ is applied to fully or partially coat the plant surface.

In a preferred embodiment, the particulate materials are contacted with a plant by applying the particulate materials as a slurry of finely divided particles in a volatile liquid such as water, a low boiling organic solvent or low boiling organic solvent/water mixtures to a plant. The slurry is made by combining the particulate materials, liquid, and other optional components (such as dispersants), and mixing the components to form the slurry. In a preferred embodiment, high shear mixing is employed to mix the components to form the slurry. In another embodiment, the particulate materials are contacted with a plant by applying the particulate materials as a dust (in a substantially dry state) to a plant.

The particulate materials useful for the purposes of this invention may be applied as a slurry of finely divided particles in a volatile liquid such as water, a low boiling organic solvent or a low boiling organic solvent/water mixture and entrained with air to create a foam. Adjuvants such as surfactants, dispersants, or spreader/stickers may be incorporated in preparing an aqueous slurry entrained with air of the particulate materials of this invention. One or more layers of this slurry can be sprayed or otherwise applied to the plant surface as a foam. The volatile liquid is preferably allowed to evaporate between coatings of a foam.

One or more layers of this slurry can be sprayed or otherwise applied to the plant surface. In another embodiment, two or more layers of this slurry can be applied to the plant surface. The volatile liquid is preferably allowed to evaporate between coatings when two or more layers are applied using a slurry. The resultant residue of the treatment according to the present invention is hydrophobic. Applying particles as a dust, although not necessarily commercially practical on a large scale due to drift and inhalation hazards, is an alternative to using a slurry for applying the particulate materials to plants.

Additives or adjuvants such as surfactants, dispersants or spreaders/stickers (adhesives) may be incorporated into the slurry of the particulate materials. For example, stickers that can be mixed with the hydrophobic particulate materials (typically in slurry form with 3% or more solids in water) to aid in spraying uniform treatments on plants include plant oil based materials such as cottonseed oil, and other commercial non-wetting stickers. In one embodiment, the amount of additives used is from about 0.01% to about 50% by weight of the particulate materials. In another embodiment, the amount of additives used is from about 0.1% to about 25% by weight of the particulate materials.

The low boiling organic liquids are preferably water-miscible and contain from 1 to about 6 carbon atoms. The term low boiling as used herein shall mean organic liquids which have a boiling point generally no more than about 100° C. These liquids promote the ability of the particulate materials to remain in a finely divided state without significant agglomeration. Examples of low boiling organic liquids include alcohols such as methanol, ethanol, propanol, i-propanol, butanol, i-butanol, and the like, ketones such as acetone, methyl ethyl ketone and the like, and cyclic ethers such as ethylene oxide, propylene oxide and tetrahydrofuran. Combinations of the above-mentioned liquids, with or without water, can also be employed. Methanol is a preferred low boiling organic liquid.

Low boiling organic liquids may be employed to facilitate applying the particulate materials by spraying onto plants. Typically, the low boiling organic liquids are used in an amount sufficient to form a dispersion of the particulate material. In one embodiment, the amount of low boiling organic liquid is from about 0% to about 30% (volume percent) of the dispersion (slurry). In another embodiment, the amount of low boiling organic liquid is from about 3% to about 5% (volume percent) of the dispersion. In yet another embodiment, the amount of low boiling organic liquid is from about 3.5% to about 4.5% (volume percent) of the dispersion.

In embodiments where a low boiling organic liquid is employed, the particulate material is preferably added to a low boiling organic liquid to form a slurry, and then the slurry is diluted with water to form an aqueous dispersion. The resulting slurry retains the particles in finely divided form wherein most (at least about 90% by weight) of the particles are dispersed to a particle size of less than about 100 microns or less.

The particulate materials particularly suitable for use in this invention are inert and nontoxic. As used herein, inert particulate materials are particles that are not phytotoxic. The particulate materials are preferably nontoxic meaning that, in the quantities needed for effective enhanced supercooling to prevent freezing damage, the particulate materials are not considered harmful to animals, the environment, the applicator and the ultimate consumer.

The invention relates to treated plants and particularly to treated horticultural crops wherein the surface of a plant is treated with one or more particulate materials. The inventive treatment does not materially affect the exchange of gases on the surface of the treated plant. The gases which pass through the particle treatment (or residue from the particle treatment) are those which are typically exchanged through the surface of living plants. Examples of such gases include water vapor, carbon dioxide, oxygen, nitrogen and volatile organics.

The following examples illustrate the methods of the present invention. Unless otherwise indicated in the following examples, in the specification and in the appended claims, all parts and percentages are by weight, temperatures are in degrees centigrade and pressures are at or near atmospheric pressure.

EXAMPLE 1

'Red Delicious' apple trees receive the following treatments: 1) application of conventional pesticide applications according to the presence of economic levels of pests using the Virginia, West Virginia and Maryland Cooperative Extension 1997 Spray Bulletin for Commercial Tree Fruit Growers publication 456-419; 2) no treatment; and 3) weekly application of Translink® 77 beginning March 11, when the plants are in a dormant state. Treatment (3) applies 25 pounds material suspended in 4 gallons of methanol and added to 100 gallons water. This treatment is applied at the rate of 125 gal/acre using an orchard sprayer. The treatments are arranged in a randomized complete block design with 4 replications and 3 trees/plot. Treatments are not irrigated and receive 21.58 cm of precipitation from May to August 30 (same year). Fruit are harvested at maturity, and fruit number are measured at harvest. Data are analyzed using Analysis of variance using a randomized complete block design.

TABLE I

| Treatment | Fruit number/tree |
| --- | --- |
| 1) Conventional | 322 |
| 2) Control | 246 |
| 3) Translink ® 77 | 382 |

The application of Translink® 77 before bud break and the occurance of a severe frost on April 9 (same year) with a minimum temperature of 20° F., moderate the frost damage as demonstrated by a larger number of fruit (382) reaching maturity compared to conventional control (322) and the non-treated control (246). The non-treated control fruit number is reduced from the conventional number by additional fruit drop caused by disease and insect damage.

EXAMPLE 2

'Seckel' pear trees receive the following treatments: 1) application of conventional pesticide applications according to the presence of economic levels of pests using the Virginia, West Virginia and Maryland Cooperative Extension 1997 Spray Bulletin for Commercial Tree Fruit Growers publication 456-419; 2) no treatment; 3) weekly application of Translink® 77 beginning on April 29; 4) weekly application of calcined kaolin (Satintone® 5HP) beginning on April 29; 5) weekly application of treated calcium carbonate (Supercoat® available from English China Clay) beginning on April 29; and 6) weekly application of Translink® 37 beginning April 29 (all April 29s of the same year). Treatments 3,5, and 6 involve applying 25 pounds material suspended in 4 gal methanol and added to 100 gal water. Treatment (4) applies 25 pounds material suspended in 100 gal water with the addition of 27 oz Ninex® MT-603 and 2 pints Toximul®. These treatments are applied at the rate of 125 gal/acre using an orchard sprayer. The treatments are arranged in a randomized complete block design with 2 replications and 4 trees/plot. A freeze of 25° F. occurs on October 23 (same year) and freeze damage of foliage is evaluated on October 28 (same year). Freeze damage is evaluated by collecting 40 leaves/plot (10 from each tree). Leaves with necrosis on the leaf margin to the midvein that extend to the abaxial side of the leaf exhibit freeze damage. Undamaged leaves lack this necrosis. Each leaf is categorized as damaged or undamaged and the percentage undamaged from each plot calculated using image analysis. Data are analyzed using Analysis of variance with a randomized complete block design.

| Treatment | Leaf damage (% of total area) |
| --- | --- |
| 1) Conventional | 63 |
| 2) Non-treated Control | 83 |
| 3) Translink ® 77 | 21 |
| 4) Satintone ® 5HB | 61 |
| 5) Supercoat ® | 18 |
| 6) Translink ® 37 | 19 |

The application of hydrophobic particles (Translink® 77, Translink® 37, and Supercoat®) reduce freezing damage compared to the non-treated control or the conventional treatment. The application of a hydrophilic material (Satintone® 5HB), does not reduce freeze damage compared to the conventional treatments.

EXAMPLE 3

A 5 μl droplet of water containing ice nucleating bacteria (*Pseudomonas syringae*) is placed on each of two tomato leaves (*Lycopersicon esculentum*). One leaf is left untreated while the other leaf is coated with a suspension of Translink® 77 before water droplet addition. The suspension is prepared by combining 9 g of Translink® 77 with 12 ml of methanol and adding this mixture to 88 ml water. The tomato leaf is sprayed to runoff with this suspension and allowed to dry. The leaves are placed in an environmental chamber and the temperature is cooled at a rate of 8° C./hour until leaf and air temperature equilibrated at 0° C. An Inframetrics 760 infrared video camera and recorder is used to record the temperature of the air, leaf and water droplet as the temperature is lowered. When ice forms, heat is released due to the heat of fusion of water and so the temperature of the freezing tissue or water rises. In the examples that follow, freezing is defined by the occurance of the exotherm associated with ice formation and a frozen tissue haves a higher temperature than an unfrozen tissue. Failure of a tissue to freeze at temperatures less than 0° C., indicates that supercooling occurs. In Example 3, the air temperature is lowered to −5.5° C.

FIG. 1 generally shows the ability of Translink® 77 to block freezing of tomato leaves. FIG. 1A shows untreated leaf (left) and Translink® 77 treated leaf (right) following exposure to −6.0° C. The untreated leaf is completely watersoaked due to freeze damage, whereas the Translink® 77 treated leaf is undamaged. In FIG. 1A, the untreated leaf on the left demonstrates watersoaking due to freeze damage, whereas the treated leaf, which is washed to remove the particles, demonstrates no freeze damage. The water droplets freeze at approximately −1.5° C.

FIG. 1B shows infrared image of untreated (left) and Translink® 77 treated (right) demonstrating freezing and the exotherm of the untreated leaf which raises the temperature of the leaf (left). The treated leaf (right) is not frozen at −3.2° C. due to enhanced supercooling. The black dot on each leaf represents the water droplet applied to the leaf surface. In FIG. 1B, the presence of a frozen droplet on the untreated leaf (left) induces freezing throughout the leaf, while the treated leaf exhibits no ice formation on the leaf. The leaf on the left is warmer due to the freezing exotherm than the leaf on the right which is supercooled but not frozen.

FIG. 1C shows infrared image of untreated (left) and Translink® 77 treated (right) demonstrating freezing and the exotherm of the untreated leaf which raises the temperature of the leaf (left). The treated leaf (right) is not frozen at −5.5° C. due to enhanced supercooling. The black dot on each leaf represents the water droplet applied to the leaf surface. FIG. 1C further demonstrates that the treated leaf (right) is cooled to −5.5° C. without ice formation while the untreated leaf (left) is frozen and has a warmer temperature (approximately −3.5° C.).

EXAMPLE 4

Whole tomato plants are treated with Translink® 77 as described in Example 3. The treated and untreated plants are sprayed with water containing ice nucleating bacteria and placed in an environmental chamber and the temperature is cooled at 8° C./hour until the plant and air temperature equilibrate at 0° C. An Inframetrics 760 infrared video camera and recorder is used to record the temperature of the air, leaf and water droplet as the temperature is lowered.

Figure 2:
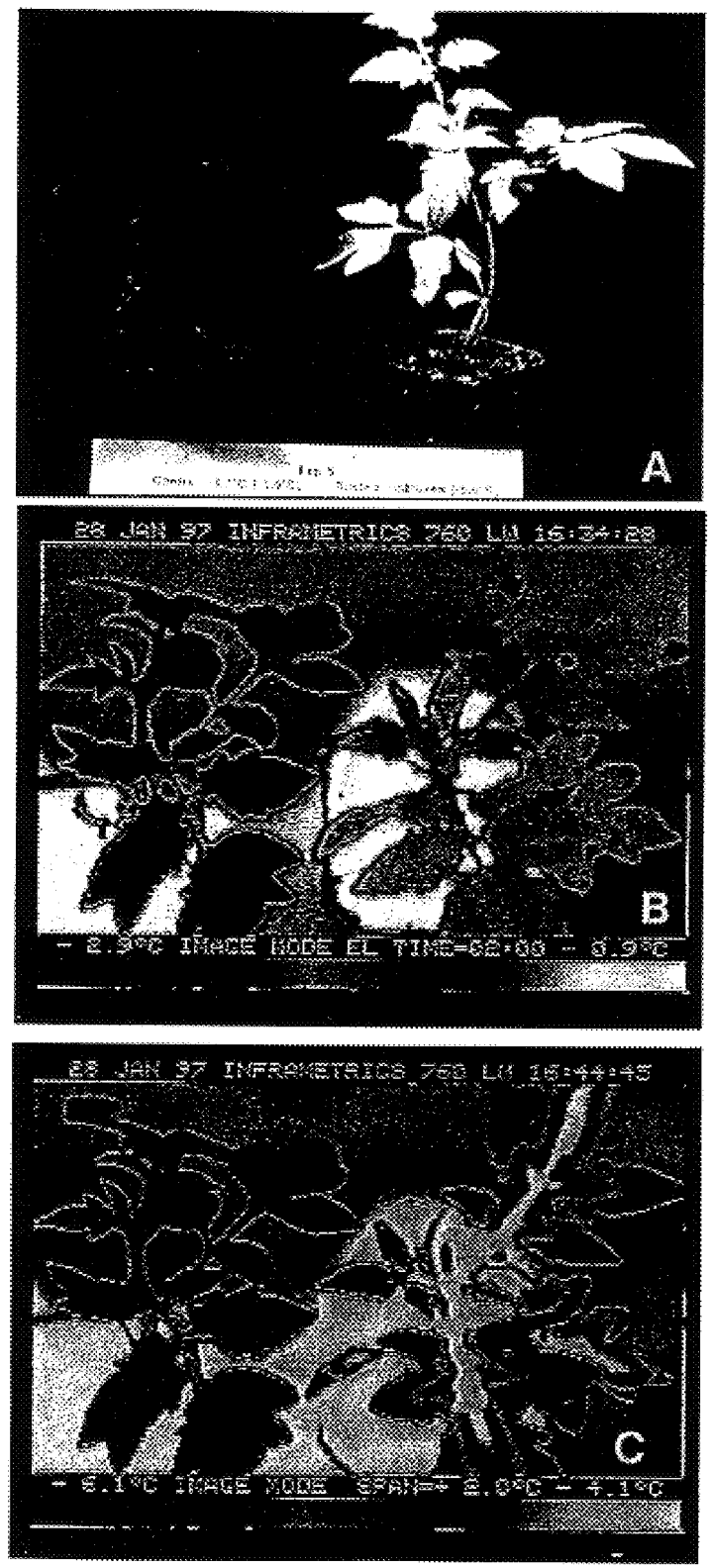

FIG. 2 generally shows the ability of Translink® 77 to block freezing of whole tomato plants. FIG. 2A shows untreated plant (left) and Translink® 77 treated plant (right) following exposure to −6.1° C. The untreated plant is completely watersoaked and flaccid due to freeze damage, whereas the Translink® 77 treated plant is undamaged. FIG. 2A illustrates that the untreated plant (left) is killed by freezing, while the treated plant (right) showed no damage after exposure to −6.1° C.

FIG. 2B shows infrared image of untreated (right) and Translink® 77 treated (left) plant demonstrating freezing and the exotherm of the untreated plant which raises the temperature of the plant (right). The treated leaf (left) is not frozen at approximately −2° C. due to enhanced supercooling. FIG. 2B illustrates that the untreated plant (right) is frozen at approximately −2° C. and is warmer than the treated plant (left) due to the freezing exotherm.

FIG. 2C shows infrared image of untreated (right) and Translink® 77 treated (left) plant demonstrating freezing and the exotherm of the untreated plant which raises the temperature of the leaf (right). The treated leaf (left) is not frozen at −6.1° C. due to enhanced supercooling. FIG. 2C illustrates that the treated plant (left) remains unfrozen at −6.1° C. compared to the untreated plant (right).

EXAMPLE 5

Two hydrophobic materials (Translink® 77 and Supercoat®), two hydrophilic materials (Satintone® 5HB, and Supermite®), and a commercial product that claims freezing control (Frost Shield®) are compared. The hydrophobic particles are prepared using 4 different methodologies: 1) the material is dusted on the plants; 2) 3 g of material are vigorously agitated with 100 ml water and sprayed on plants while being agitated; 3) 3 g of material are vigorously agitated with 100 ml water containing 0.5 ml cottonseed oil, and the suspension sprayed on the plants while being agitated; and 4) 3 g of material are mixed with 4 ml of methanol and that mixture is added to 96 ml water. The hydrophilic materials are prepared and applied similar to 1), 2) and 3) above. One leaf is left untreated while the other leaf is coated with one of the material treatments. The tomato leaf is sprayed to runoff with the suspension and allowed to dry. A 5 pi droplet of water containing ice nucleating bacteria (*Pseudomonas syringae*) is placed on each of two tomato leaves (*Lycopersicon esculentum*). The leaves are placed in an environmental chamber and the temperature is cooled at 8° C./hour until leaf and air temperature equilibrate at 0° C. An Inframetrics 760 infrared video camera and recorder is used to record the temperature of the air, leaf and water droplet as the temperature is lowered. The air temperature is lowered to −5.0° C. In all cases, hydrophobic particle treated leaves do not freeze while the untreated leaves and the hydrophilic treated leaves freeze.

Figure 15:
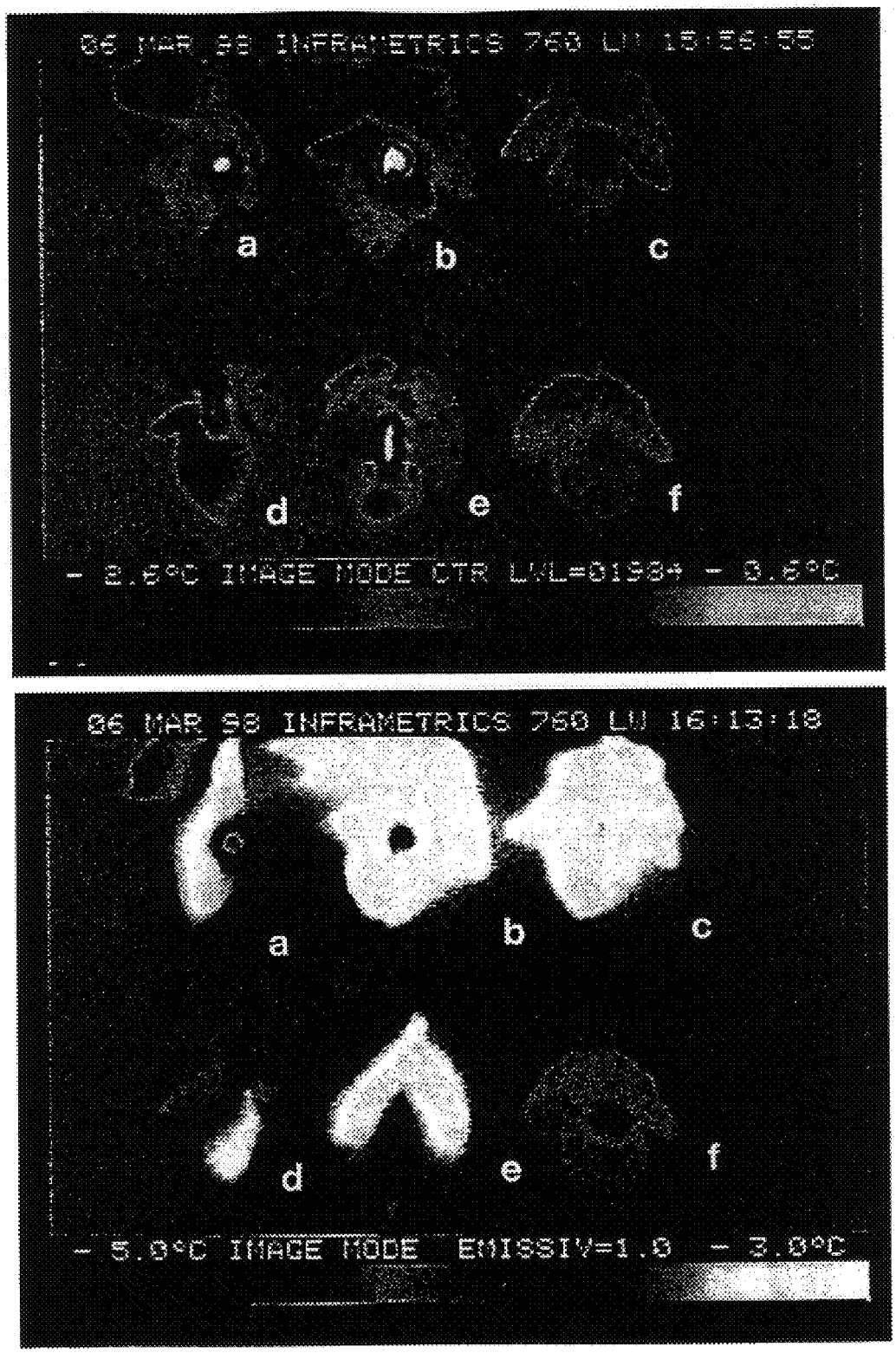

FIGS. 3–6 illustrate the coverage on the leaf surface with the various materials and formulations. Note that incomplete coverage does occur in the hydrophobic treatments but this does not reduce supercooling in the range of 0 to −5.0° C. FIGS. 7–14 illustrate that hydrophobic particle treated leaves do not freeze while the untreated leaves freeze. FIGS. 15 and 16 illustrate that hydrophilic particle treated leaves and FrostShield® (4 oz of FrostShield®/2 quarts of water applied to drip) freeze similar to the untreated leaves.

Figure 3:
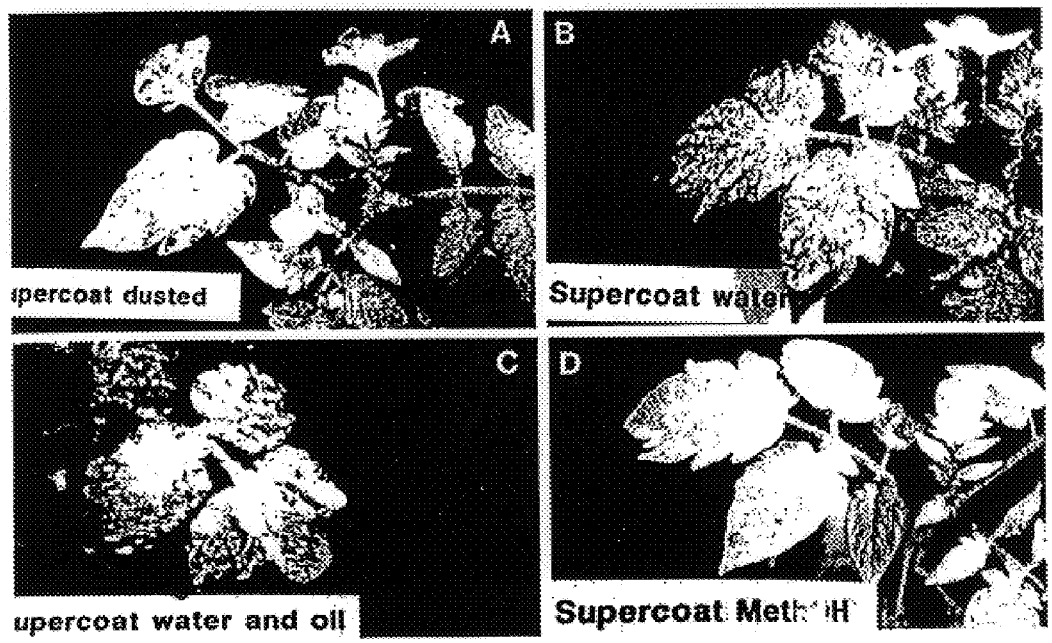

FIG. 3 generally shows the evaluation of Supercoat® formulations. FIG. 3A shows a plant treated with Supercoate applied as a dust, FIG. 3B shows a plant treated with Supercoat® applied in a water suspension, FIG. 3C shows a plant treated with Supercoat® applied in a water suspension with 0.5% cottonseed oil, and FIG. 3D shows a plant treated with 3% Supercoat® initially suspended in methanol and the suspension added to water.

Figure 4:

FIG. 4 generally shows the evaluation of Translink® 77 formulations. FIG. 4A shows a plant treated with dust formulation, FIG. 4B shows a plant treated with Translink® 77 applied in a water suspension, FIG. 3C shows a plant treated with Translink® 77 applied in a water suspension with 0.5% cottonseed oil, and FIG. 3D shows a plant treated with Translink® 77 suspended in methanol and the suspension added to water.

Figure 5:
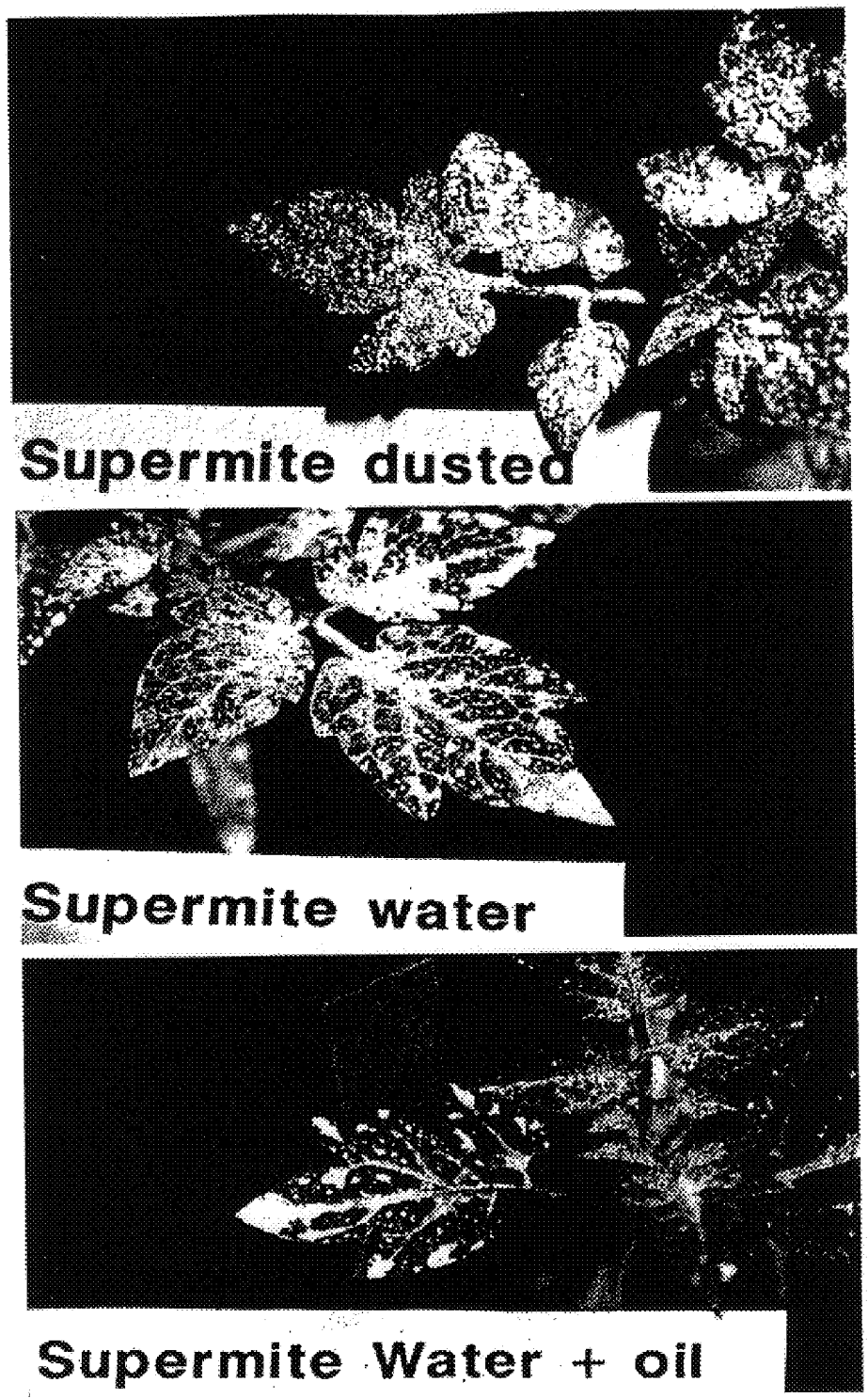

FIG. 5 generally shows the evalution of Supermite® formulations. The top-plant is treated with dust formulation, the middle-plant is treated with Supermite® applied in a water suspension, and the bottom-Plant is treated with Translink® 77 applied in a water suspension with 0.5% cottonseed oil.

Figure 6:
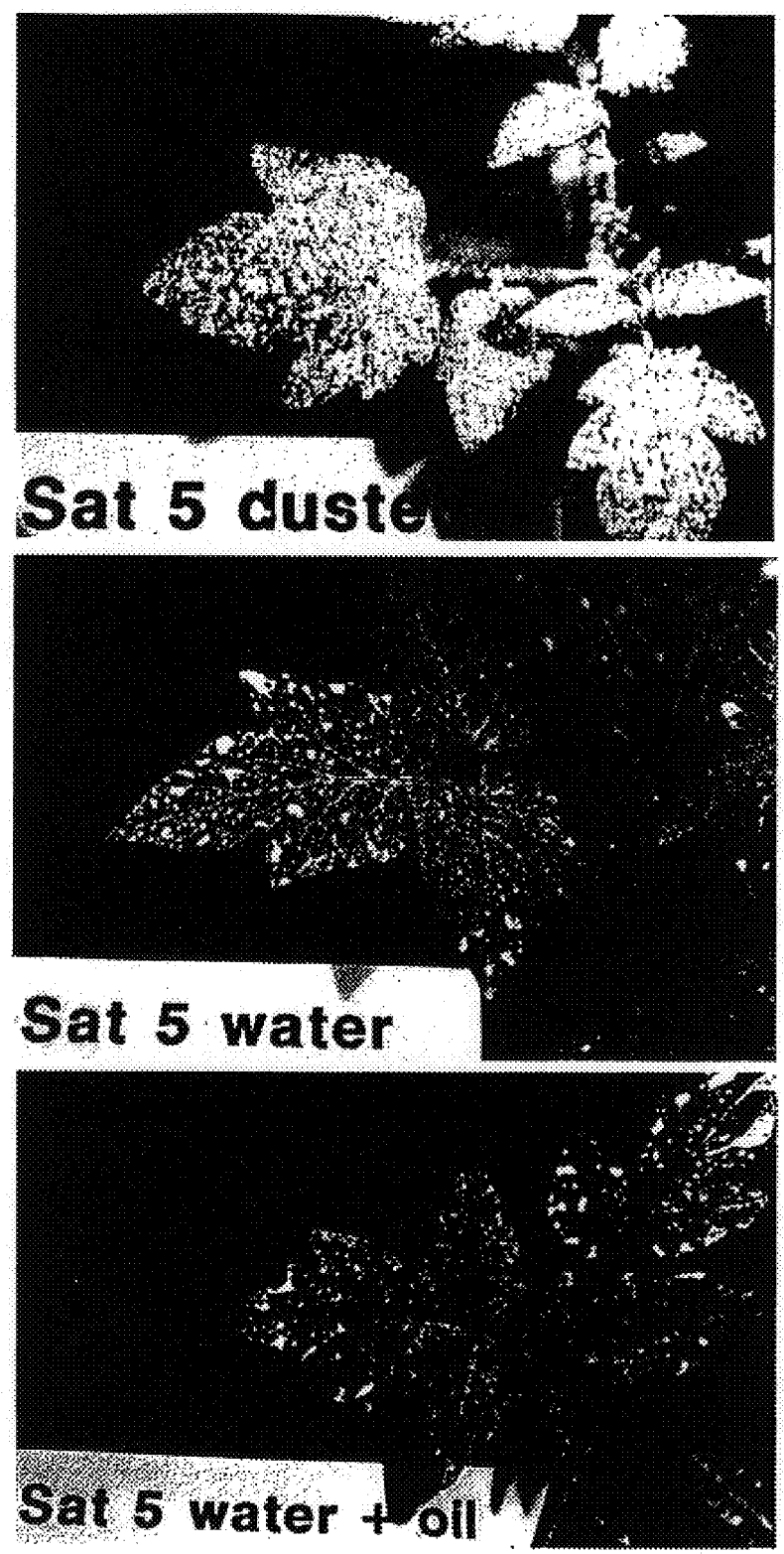

FIG. 6 generally shows the evaluation of Satintone 5HB® formulations. The top-plant is treated with dust formulation, the middle-plant is treated with Satintone 5HB® applied in a water suspension, and the bottom-Plant is treated with Satintone 5HB® applied in a water suspension with 0.5% cottonseed oil.

Figure 7:
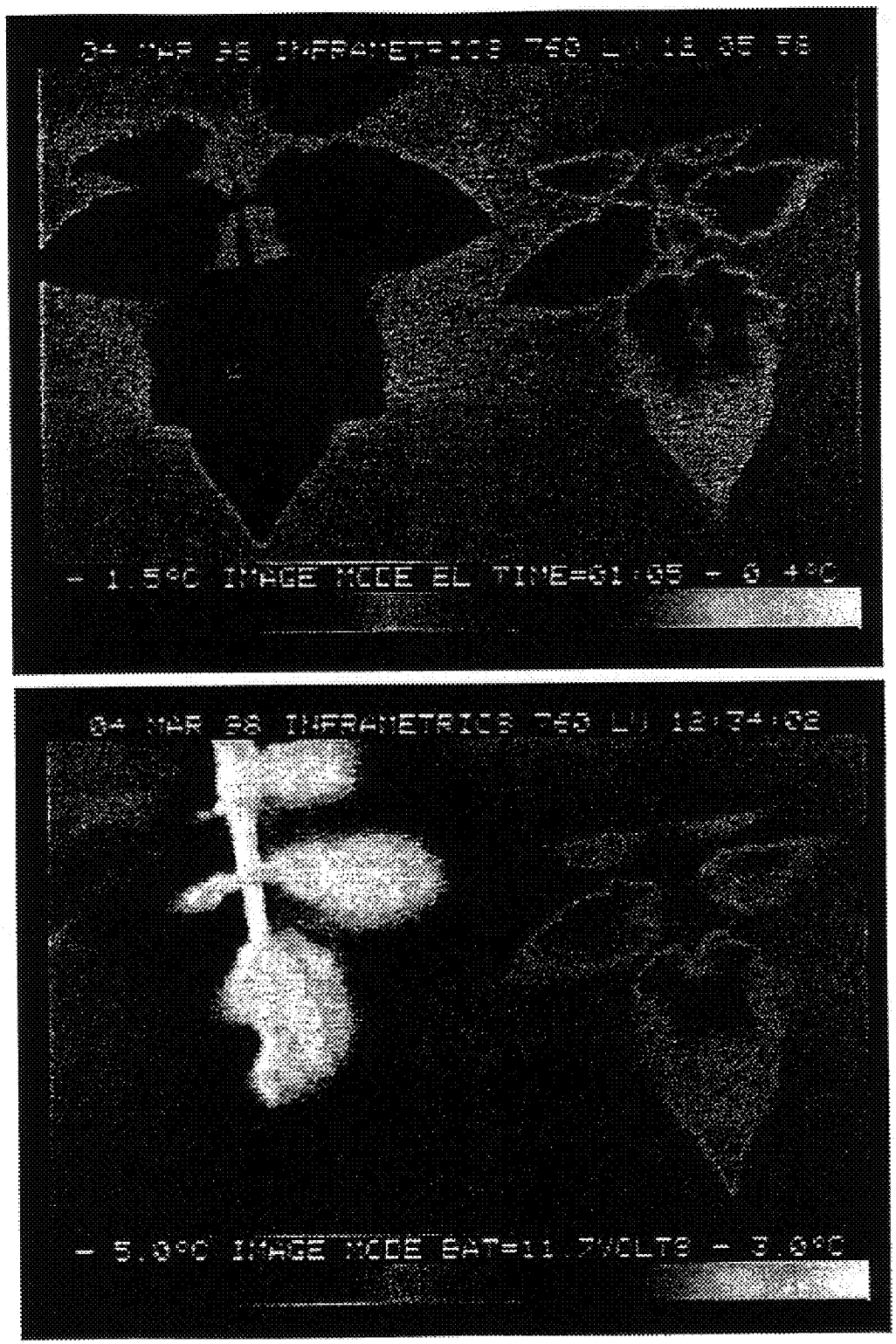

FIG. 7 generally shows infrared images of plants treated with Supercoat® applied as a dust. The top- untreated leaf (left) and treated leaf (right) are shown during a freezing protocol. Plants are unfrozen. The bottom-untreated leaf (left) and treated leaf (right) are shown during a freezing event. The untreated is frozen and demonstrates a freezing exotherm, while the treated leaf remains unfrozen at −5.0° C.

The circular dots on each leaf are water droplets containing ice nucleating bacteria.

FIG. 8 generally shows infrared images of plants treated with Supercoat® applied as solids (3% w/w) suspended in methanol and water. The top-untreated leaf (left) and treated leaf (right) are shown during a freezing protocol. Plants are unfrozen. The bottom-untreated leaf (left) and treated leaf (right) are shown during a freezing event. The untreated has frozen and demonstrates a freezing exotherm, while the treated leaf remains unfrozen at −2.5° C. The circular dots on each leaf are water droplets containing ice nucleating bacteria.

FIG. 9 generally shows infrared images of plants treated with Supercoat® applied in water with 0.5% cottonseed oil. The top-untreated leaf (left) and treated leaf (right) during a freezing protocol. Plants are unfrozen. The bottom-untreated leaf (left) and treated leaf (right) are shown during a freezing event. The untreated is frozen and demonstrates a freezing exotherm, while the treated leaf remains unfrozen at 4.5° C. The circular dots on each leaf are water droplets containing ice nucleating bacteria.

FIG. 10 generally shows infrared images of plants treated with Supercoat® applied in water. The top-untreated leaf (left) and treated leaf (right) are shown during a freezing protocol. Plants are unfrozen. The bottom-untreated leaf (left) and treated leaf (right) are shown during a freezing event. The untreated is frozen and demonstrates a freezing exotherm, while the treated leaf remains unfrozen at −2.8° C. The circular dots on each leaf are water droplets containing ice nucleating bacteria.

Figure 11:
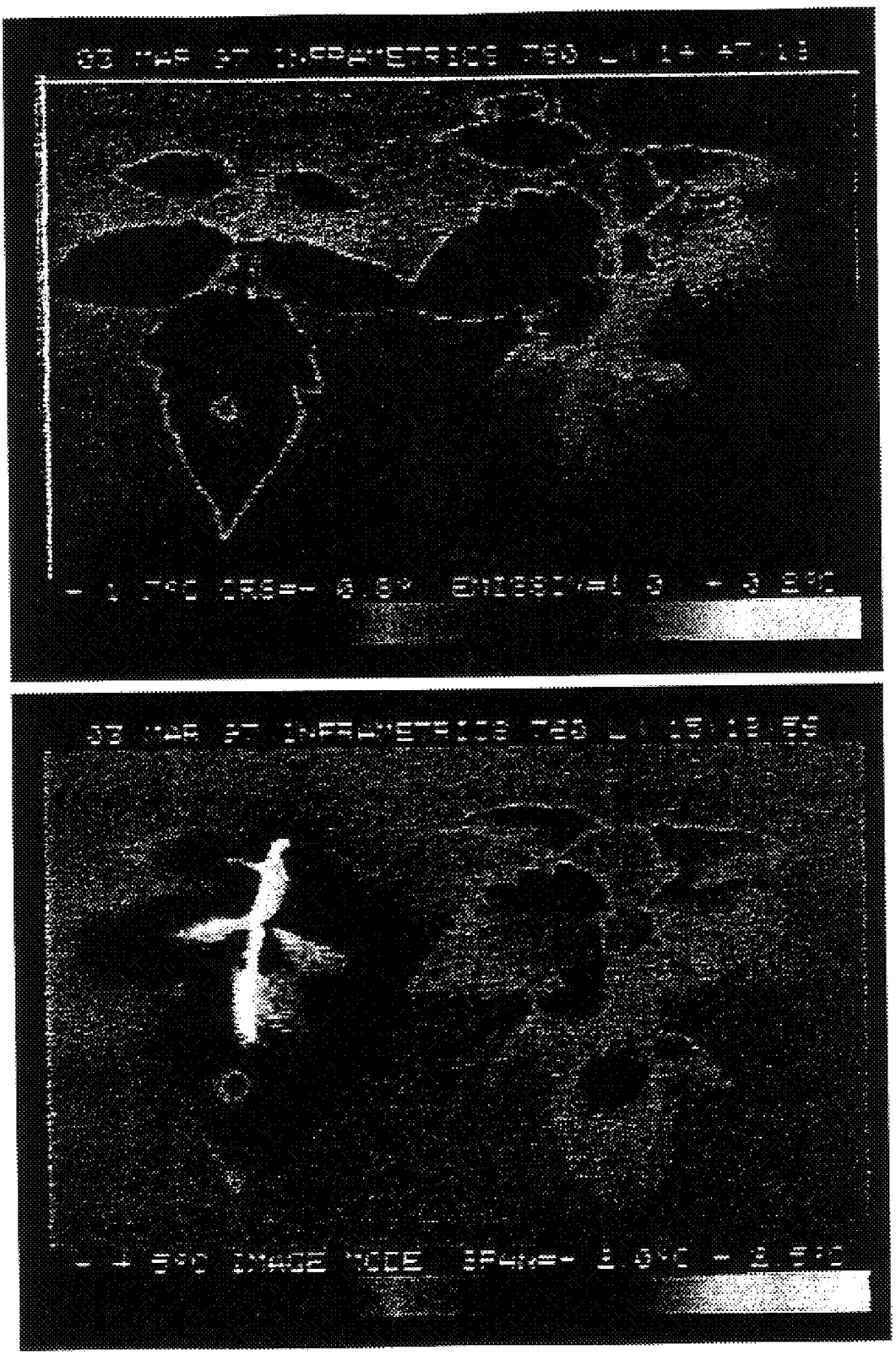

FIG. 11 generally shows infrared images of plants treated with Translink® 77 suspended in methanol and added to water. The top-untreated leaf (left) and treated leaf (right) are shown during a freezing protocol. Plants are unfrozen. The bottom-untreated leaf (left) and treated leaf (right) are shown during a freezing event. The untreated is frozen and demonstrates a freezing exotherm, while the treated leaf remains unfrozen at −4.5° C. The circular dots on each leaf are water droplets containing ice nucleating bacteria.

Figure 12:
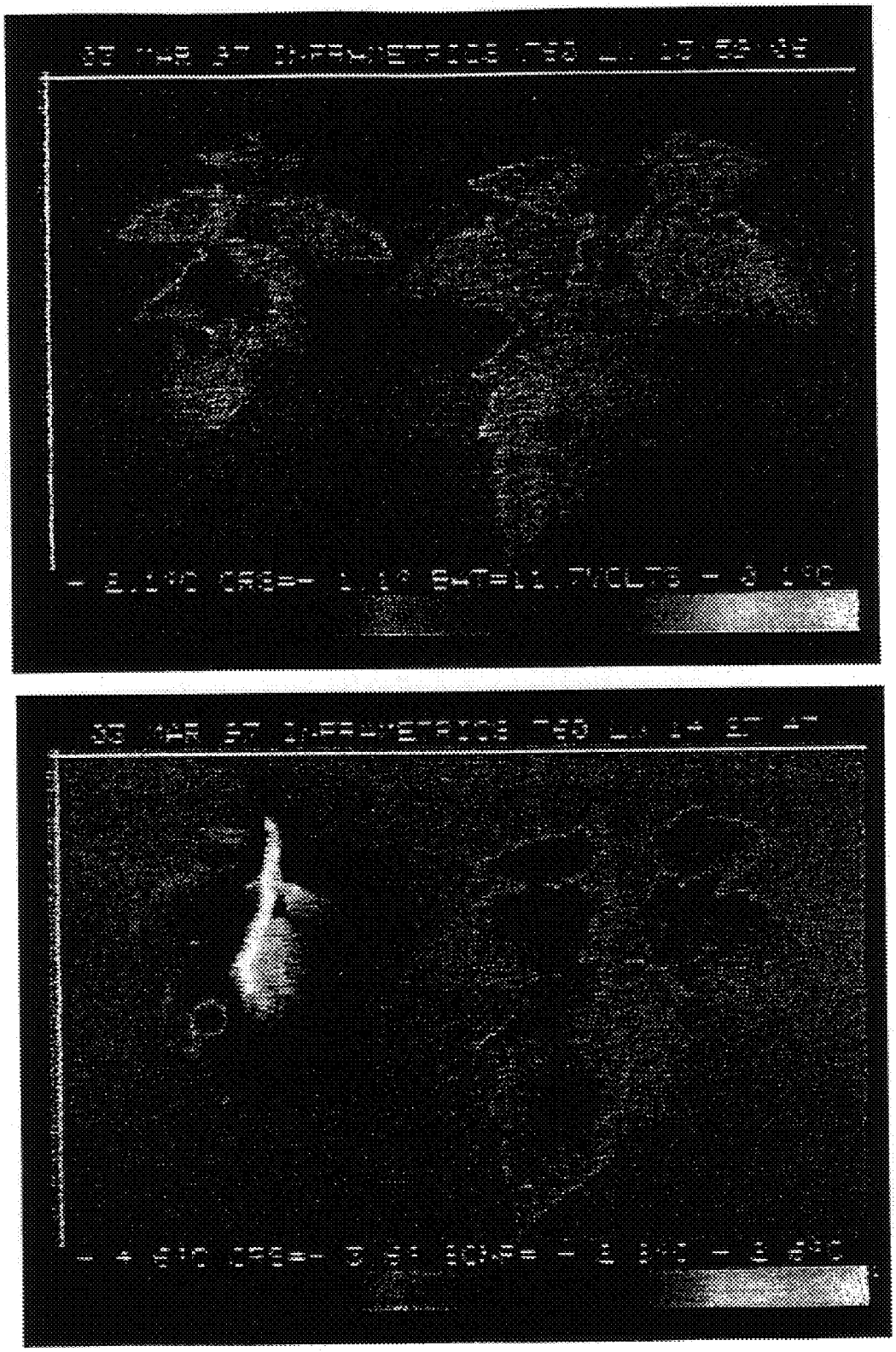

FIG. 12 generally shows infrared images of plants treated with Translink® 77 applied in water with 0.5% cottonseed oil. The top-untreated leaf (left) and treated leaf (right) are shown during a freezing protocol. Plants are unfrozen. The bottom-untreated leaf (left) and treated leaf (right) during a freezing event. The untreated is frozen and demonstrates a freezing exotherm, while the treated leaf remains unfrozen at −4.5° C. The circular dots on each leaf are water droplets containing ice nucleating bacteria.

Figure 13:
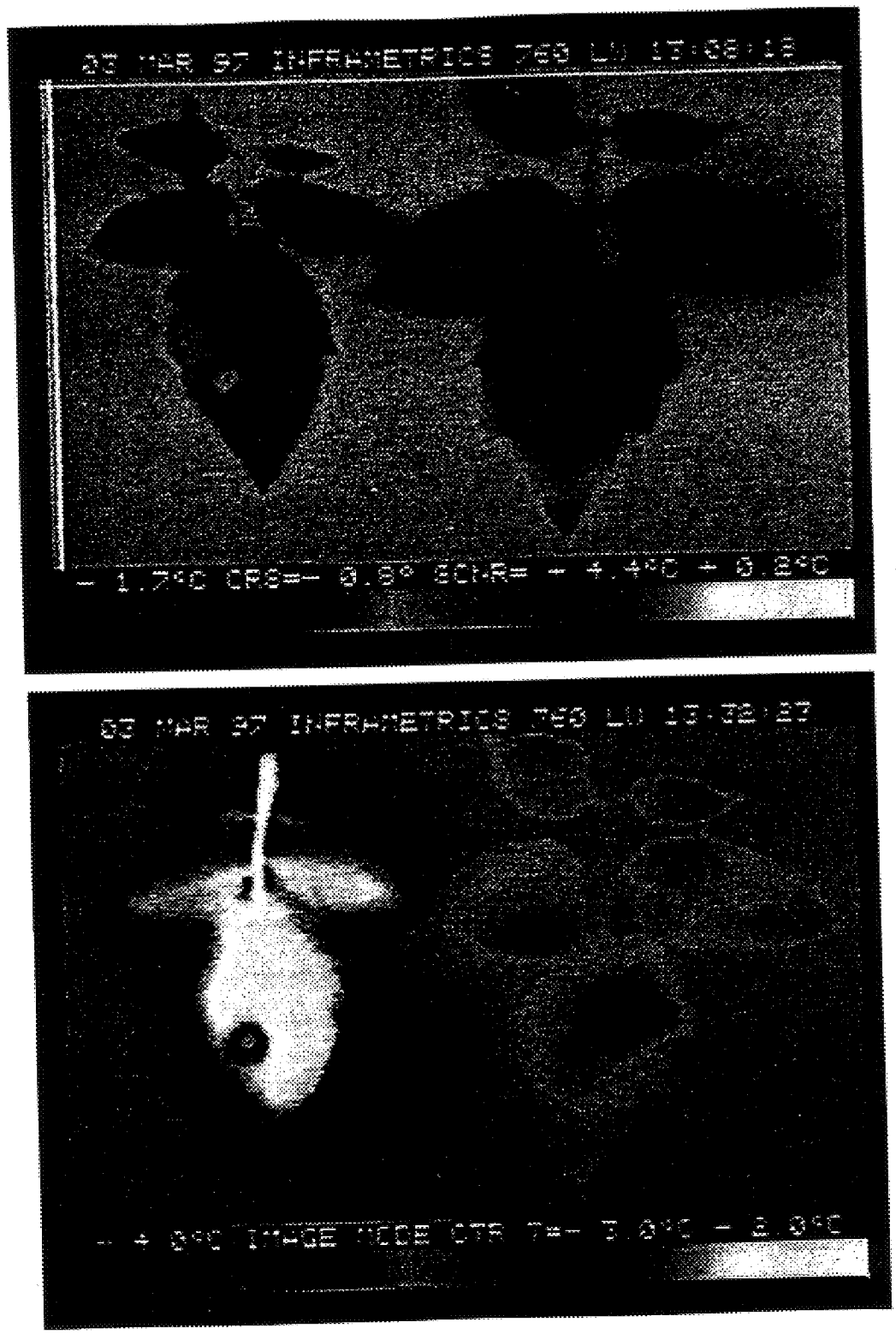

FIG. 13 generally shows infrared images of plants treated with Translink® 77 applied in water. The top-untreated leaf (left) and treated leaf (right) are shown during a freezing protocol. Plants are unfrozen. The bottom-untreated leaf (left) and treated leaf (right) are shown during a freezing event. The untreated is frozen and demonstrates a freezing exotherm, while the treated leaf remains unfrozen at −4° C. The circular dots on each leaf are water droplets containing ice nucleating bacteria.

FIG. 14 generally shows infrared images of plants treated with Translink® 77 applied as a dust. The top-untreated leaf (left) and treated leaf (right) are shown during a freezing protocol. Plants are unfrozen. The bottom-untreated leaf (left) and treated leaf (right) are shown during a freezing event. The untreated is frozen and demonstrates a freezing exotherm, while the treated leaf remains unfrozen at −5° C. The circular dots on each leaf are water droplets containing ice nucleating bacteria.

FIG. 15 generally shows infrared images of tomato leaves during a freezing protocol. In the top, early stages of freezing are shown when actual freezing does not yet occur. Leaves with (a) untreated, (b) FrostShield®, (c) Supermite® applied as a dust, (d) Supermite® applied in water, (e) Supermite® applied in water with 0.5% cottonseed oil, (f) Translink® 77 suspended in methanol and water are shown. In the bottom, all leaves are frozen except Translink® 77 which is unfrozen at 4.2° C.

FIG. 16 generally shows infrared images of tomato leaves during a freezing protocol. In the top, early stages of freezing are shown when actual freezing does not yet occur. Leaves with (a) untreated, (b) FrostShield®, (c) Satintone 5HB® applied as a dust, (d) Satintone 5HB® applied in water, (e) Satintone 5HB® applied in water with 0.5% cottonseed oil, (f) Translink® 77 suspended in methanol and water are shown. In the bottom, all leaves are frozen except Translink® 77 which is unfrozen at −4.2° C.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A method for enhancing supercooling of a plant to temperatures below about −2° C., comprising:
preventing the formation of ice crystals adjacent the plant by forming a substantially continuous hydrophobic membrane of particulate materials on portions of the plant capable of supporting droplets of water, the particulate material having a particle size distribution wherein up to about 90% by weight of the particles have a particle size of about 100 $\mu$m or less, and the substantially continuous hydrophobic membrane has a thickness from about 1 $\mu$m to about 1,000 $\mu$m, and wherein the particulate material comprises a hydrophilic core and a hydrophobic outer surface and the hydrophilic core comprises at least one of calcium carbonate, mica, talc, kaolin, bentonite, pyrophillite, dolomite, silica, feldspar, sand, quartz, chalk, limestone, diatomaceous earth, baryte, aluminum trihydrate, and titanium dioxide.

2. The method of claim 1, wherein the particulate material prevents water from accumulating on the surface of the plant.

3. The method of claim 1, wherein the particulate material prevents propagation of ice through a plant cuticle, a stomate or a lesion in the cuticle of the plant.

4. The method of claim 1, wherein the particulate material has a particle size distribution wherein up to about 90% by weight of the particles have a particle size of about 10 $\mu$m or less.

5. The method of claim 1, wherein the hydrophilic core comprises at least one of hydrous kaolin, calcined kaolin, precipitated calcium carbonate, and pyrogenic silica.

6. The method of claim 1, wherein the hydrophobic outer surface comprises at least one of organic titanates, organic zirconate or aluminate coupling agents, organofunctional silanes, modified silicone fluids and fatty acids and salts thereof.

7. The method of claim 1, wherein the plant is at least one of an actively growing agricultural crop, a fruiting agricultural crop, an actively growing ornamental crop, and a fruiting ornamental crop.

8. The method of claim 1, wherein the plant is at least one of fruits, vegetables, trees, flowers, grasses, roots, seeds, landscape and ornamental plants.

9. The method of claim 1, wherein the particulate material has a median individual particle size of about 3 µm or less.

10. The method of claim 1, wherein the hydrophilic core comprises at least one of calcium carbonate and calcined kaolin.

11. The method of claim 1 wherein the particulate material is comprises at least one of hydrophobic treated calcium carbonate and hydrophobic treated calcined kaolin.

12. A method for enhancing the supercooling of a horticultural crop to temperatures below about −3° C., comprising:

preventing the formation of ice crystals adjacent the horticultural crop by applying a slurry comprising particulate materials and a liquid on portions of the horticultural crop capable of supporting droplets of water; and permitting the liquid to evaporate thereby forming a substantially continuous hydrophobic membrane of particulate materials on the horticultural crop, the particulate material having a particle size distribution wherein up to about 90% by weight of the particles have a particle size of about 10 µm or less, and the substantially continuous hydrophobic membrane has a thickness from about 3 µm to about 1,000 µm.

13. The method of claim 1, wherein the particulate materials are applied one or more times during the growing season of said horticultural crop.

14. The method of claim 1, wherein the particulate material has a particle size distribution wherein up to about 90% by weight of the particles have a particle size of about 3 µm or less.

15. The method of claim 12 wherein the particulate material comprises a hydrophilic core and a hydrophobic outer surface.

16. The method of claim 15, wherein the hydrophilic core comprises at least one of calcium carbonate, mica, kaolin, bentonite, pyrophyllite, silica, feldspar, sand, quartz, chalk, limestone, diatomaceous earth, baryte, aluminum trihydrate, and titanium dioxide.

17. The method of claim 12, wherein the substantially continuous hydrophobic membrane comprises noncontinuous areas having an average size of less than about 100 µm.

18. A method for enhancing the supercooling of a horticultural crop to temperatures below about −4° C., comprising:

preventing the formation of ice crystals adjacent the horticultural crop by applying a slurry comprising particulate materials, a liquid, and an adjuvant on portions of the horticultural crop capable of supporting droplets of water; and permitting the liquid to evaporate thereby forming a substantially continuous hydrophobic membrane of particulate materials on the horticultural crop, the particulate material having a particle size distribution wherein up to about 90% by weight of the particles have a particle size of about 10 µm or less, and the substantially continuous hydrophobic membrane comprises from about 25 to about 5000 micrograms of particulate material/cm$^2$ of horticultural crop surface.

19. The method of claim 18, wherein the particulate material prevents water from accumulating on the surface of the plant.

20. The method of claim 18, wherein the particulate material has a particle size distribution wherein up to about 90% by weight of the particles have a particle size of about 1 µm or less.

21. The method of claim 18, wherein the particulate material comprises a hydrophilic core and a hydrophobic outer surface.

22. The method of claim 18, wherein the hydrophilic core comprises at least one of calcium carbonate, mica, kaolin, bentonite, pyrophyllite, silica, feldspar, sand, quartz, chalk, limestone, diatomaceous earth, baryte, aluminum trihydrate, and titanium dioxide.

23. The method of claim 18, wherein the substantially continuous hydrophobic membrane comprises noncontinuous areas having an average size of less than about 100 µm.

* * * * *